United States Patent
Mickevicius et al.

(10) Patent No.: US 12,076,130 B2
(45) Date of Patent: Sep. 3, 2024

(54) METHOD FOR REAL-TIME MOTION MONITORING AND DOSE ACCUMULATION IN MAGNETIC RESONANCE GUIDED THERAPIES USING SIMULTANEOUS ORTHOGONAL PLANE IMAGING

(71) Applicant: THE MEDICAL COLLEGE OF WISCONSIN, INC., Milwaukee, WI (US)

(72) Inventors: Nikolai Mickevicius, Milwaukee, WI (US); Eric Paulson, Jackson, WI (US)

(73) Assignee: The Medical College of Wisconsin, Inc., Milwaukee, WI (US)

(*) Notice: Subject to any disclaimer, the term of this patent is extended or adjusted under 35 U.S.C. 154(b) by 925 days.

(21) Appl. No.: 16/982,821

(22) PCT Filed: Mar. 20, 2019

(86) PCT No.: PCT/US2019/023266
§ 371 (c)(1),
(2) Date: Sep. 21, 2020

(87) PCT Pub. No.: WO2019/183287
PCT Pub. Date: Sep. 26, 2019

(65) Prior Publication Data
US 2021/0052186 A1    Feb. 25, 2021

Related U.S. Application Data

(60) Provisional application No. 62/645,787, filed on Mar. 20, 2018, provisional application No. 62/645,800, filed on Mar. 21, 2018.

(51) Int. Cl.
*A61B 5/055*    (2006.01)
*G01R 33/48*    (2006.01)
(Continued)

(52) U.S. Cl.
CPC .......... *A61B 5/055* (2013.01); *G01R 33/4808* (2013.01); *G01R 33/4835* (2013.01);
(Continued)

(58) Field of Classification Search
CPC ............... A61B 5/055; G01R 33/4808; G01R 33/4835; G01R 33/5611; G01R 33/56509;
(Continued)

(56) References Cited

U.S. PATENT DOCUMENTS

| | | | | |
|---|---|---|---|---|
| 5,749,834 A | * | 5/1998 | Hushek ............... | G01R 33/4835 324/309 |
| 2012/0165652 A1 | * | 6/2012 | Dempsey ............. | A61N 5/1067 600/410 |

(Continued)

FOREIGN PATENT DOCUMENTS

| WO | 2010/008097 A1 | 1/2010 |
| WO | 2017/173437 A1 | 10/2017 |

OTHER PUBLICATIONS

Mickevicius NJ, Paulson ES. Simultaneous orthogonal plane imaging. Magn Reson Med. Nov. 2017;78(5):1700-1710. doi: 10.1002/mrm.26555. Epub Dec. 4, 2016. PMID: 27917527. (Year: 2016).*

(Continued)

*Primary Examiner* — Patrick Fernandes
*Assistant Examiner* — Nicholas A Robinson
(74) *Attorney, Agent, or Firm* — Quarles & Brady LLP

(57) ABSTRACT

Systems and methods for providing image guidance for motion tracking and compensation in magnetic resonance imaging ("MRI") guided therapies, such as MRI-guided radiation therapies using an MR-linac or other MRI-guided radiation therapy system, are described. Simultaneous orthogonal plane imaging ("SOPI") is used to acquire images from a first slice that remains static throughout the acquisition, and from a plurality of slices that are orthogonal (Continued)

to the first slice. This first slice can be referred to in some instances as a "tracking" or "navigator" slice, and the plurality of slices that are orthogonal to the first slice can be referred to as "imaging" slices. The tracking slice images can be used to estimate motion of the subject that occurred during the data acquisition, and to track the position of targets (e.g., anatomical targets) during the delivery of radiation treatment.

24 Claims, 14 Drawing Sheets

(51) Int. Cl.
*G01R 33/483* (2006.01)
*G01R 33/561* (2006.01)
*G01R 33/565* (2006.01)
*G01R 33/567* (2006.01)

(52) U.S. Cl.
CPC .... *G01R 33/5611* (2013.01); *G01R 33/56509* (2013.01); *G01R 33/5676* (2013.01)

(58) Field of Classification Search
CPC ............ G01R 33/5676; G01R 33/5607; G01R 33/56325
See application file for complete search history.

(56) References Cited

U.S. PATENT DOCUMENTS

| | | | | |
|---|---|---|---|---|
| 2014/0035576 | A1* | 2/2014 | Li | G01R 33/5619 324/309 |
| 2014/0286589 | A1* | 9/2014 | Amon | H04N 19/51 382/238 |
| 2016/0361569 | A1* | 12/2016 | Sayeed | A61N 5/1038 |
| 2017/0146631 | A1 | 5/2017 | Beck et al. | |
| 2017/0157426 | A1* | 6/2017 | Buchsbaum | A61N 5/1067 |
| 2017/0169586 | A1* | 6/2017 | Ding | G06T 11/003 |
| 2018/0168534 | A1* | 6/2018 | Desponds | A61B 6/0407 |
| 2018/0353098 | A1* | 12/2018 | Ye | G01R 33/4818 |

OTHER PUBLICATIONS

Kolbitsch, C.P., "Advanced techniques for cardiovascular magnetic resonance imaging in cases of irregular motion", 2012, pp. 1-191, https://kclpure.kcl.ac.uk/portal/files/12927436/Studentthesis-Christoph_Kolbitsch_2012.pdf.

Mickevicius, N.J., et al., "Simultaneous Orthogonal Plane Imaging", Magnetic Resonance in Medicine, 78:1700-1710 (2017).

Von Siebenthal, M., et al., "4D MR imaging of respiratory organ motion and its variability", Phys. Med. Biol. 52 (2007) 1547-1564.

Lin, W., et al., "Real-Time Motion Correction in Two Dimensional Multislice Imaging with Through-Plane Navigator", Magnetic Resonance in Medicine 71:1995-2005 (2014).

Tryggestad, E., et al., "4D tumor centroid tracking using orthogonal 2D dynamic MRI: Implications for radiotherapy planning", Med. Phys. 40(9), Sep. 2013, 091712-1-091712-12.

Hoinkiss, D.C., et al., "A Novel Approach to Prospective Motion Correction Using Multi-Slice-to-Volume Registration", Proc. Inc. Soc. Mag. Reson Med. 25th Annual Meeting & Exhibition, No. 299, Apr. 7, 2017.

Mickevicius, N.J., et al., "Simultaneous Motion Monitoring and Truth-In-Delivery Analysis Imaging Framework for MR-guided Radiotherapy", ARXIV.org, Cornell University Library, Jun. 20, 2018, 26 pages.

* cited by examiner

- - - - Navigator Slice      ·········· Imaging Slice      ········ Prescribed Slice

- - - - Navigator Slice      ·········· Imaging Slice      ········ Prescribed Slice

METHOD FOR REAL-TIME MOTION MONITORING AND DOSE ACCUMULATION IN MAGNETIC RESONANCE GUIDED THERAPIES USING SIMULTANEOUS ORTHOGONAL PLANE IMAGING

CROSS-REFERENCE TO RELATED APPLICATIONS

This application is a national stage filing under 35 U.S.C. 371 of International Application No. PCT/US2019/023266, filed Mar. 20, 2019, which claims the benefit of U.S. Provisional Patent Application Ser. No. 62/645,787, filed on Mar. 20, 2018, and entitled "METHOD FOR MEASURING DOSE ACCUMULATION USING SIMULTANEOUS ORTHOGONAL PLANE MAGNETIC RESONANCE IMAGING," and of U.S. Provisional Patent Application Ser. No. 62/645,800, filed on Mar. 21, 2018, and entitled "METHOD FOR REAL-TIME MOTION MONITORING AND DOSE ACCUMULATION IN MAGNETIC RESONANCE GUIDED THERAPIES USING SIMULTANEOUS ORTHOGONAL PLANE IMAGING," the contents of each are herein incorporated by reference in their entirety.

BACKGROUND

Adaptive radiation therapy ("ART") is a promising approach to maintain prescribed target coverage while handling anatomic and motion variability. In online ART, the radiation therapy ("RT") plan for each fraction is adapted based on interfractional changes in anatomy that occur from day to day. From the measured changes in daily anatomy detected with a volumetric image (typically CT), the original reference treatment plan is altered to maximize dose to the target while minimizing dose to nearby organs-at-risk ("OAR").

Intrafractional variations present additional challenges. In particular, large translations, rotations, and deformations occurring due to respiration, peristalsis, organ filling, or muscle relaxation can cause deviations between the planned and delivered dose. Respiratory gating is one approach to compensate for respiratory motion. On conventional linear accelerators, a one-dimensional motion surrogate signal (e.g. from a respiratory bellows or reflective marker placed on the chest of a patient) is monitored over time. When the signal falls within a pre-determined threshold, the beam is turned on. On state-of-the-art hybrid MR imaging and RT treatment devices, gating can be based on rapidly acquired 2D cross-sectional images intersecting the target and/or OAR. The MR images reduce the uncertainty in estimating target position from motion surrogate signals.

The use of 4D CT or MR imaging (3D+respiratory phase) during simulation can also help to account for intrafraction motion. An internal target volume ("ITV") may be created to encompass the total extent of the gross target volume ("GTV") throughout the respiratory cycle. The GTV moves within this ITV while the beam is on, resulting in larger irradiated volumes that include OAR.

More recently, the use of pre-beam 4D-MRI has been proposed to be used in conjunction with beam-on cine imaging to accumulate dose on MR-guided RT systems. In this approach, a motion model is generated from the 4D-MRI and dynamically updated throughout the treatment fraction through deformable registration with the cine images. The dynamic update of the motion model facilitates generation of a synthetic 3D volume at the frame rate of the cine images, while also permitting control for deviations from the average respiratory cycle determined from the pre-beam 4D-MRI. While this is a powerful method, an approach that does not depend on the accuracy of deformable registration is desired.

A plethora of methods exist for acquiring 4D-MRI. They can include 2D multi-slice approaches or volumetric (e.g., 3D) approaches. Most commonly, the data sorting is performed retrospectively. A rapidly emerging 4D-MRI approach is that of a 3D stack-of-stars radial acquisition with a golden angle increment. This technique permits the use of combined parallel imaging and sparsity constraints to reconstruct high quality 3D volumes at multiple respiratory phases from highly undersampled acquisitions with durations under two minutes.

If the use of deformable registration is to be avoided, dynamically updating 4D-MRIs must be reconstructed throughout the treatment fraction. The simplest solution would be to acquire continuous 3D stack-of-stars data during beam-on and reconstruct 4D-MRI epochs that account for short-term variations in respiratory pattern or physiological effects such as organ filling. However, with this approach, the ability to acquire real-time images for instantaneous determination of the current respiratory phase is lost, as is the ability to track or perform respiratory gating based on 2D images.

The 2D multislice methods of building respiratory phase-resolved 3D volumes have also proven to be effective. In some implementations of multislice 2D 4D-MRI, the acquisition of a 2D navigator slice and 2D imaging slice were acquired in an interleaved fashion. The position of the navigator slice remains constant while the imaging slice cycles through other spatial positions within the volume. The imaging slices are subsequently binned into the appropriate respiratory phase based on the position of tracking markers or some form of similarity metric between repetitions of the navigator slice.

The method of 2D imaging for 4D-MRI was improved via the use of simultaneous multislice ("SMS") imaging. A recent study proposed the use of parallel imaging with controlled aliasing (e.g., CAIPIRINHA) to separate simultaneously acquired data from a sagittal navigator slice and a sagittal imaging slice. This proved to be more efficient than the conventional method of interleaving data from the navigator and imaging slices. Because data from a navigator slice are continually acquired, it is possible to determine the appropriate respiratory phase volume from a 4D-MRI on which dose can be calculated. The navigator slice could also be chosen to intersect the target for tracking or respiratory gating purposes.

SUMMARY OF THE DISCLOSURE

The present disclosure addresses the aforementioned drawbacks by providing a method for producing images of a subject using a magnetic resonance imaging ("MRI") system. Data are acquired from a volume in a subject with an MRI system using a pulse sequence in which the data are simultaneously acquired in each repetition time period of the pulse sequence as first data from a first slice and second data from a second slice that is orthogonal to the first slice. The pulse sequence is repeated for a number of repetition time periods during which a position of the first slice remains static and a position of the second slice is changed such that the second data are acquired from different slices in the volume that are each orthogonal to the first slice. A series of first images is reconstructed from the first data, and a series of second images from the second data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
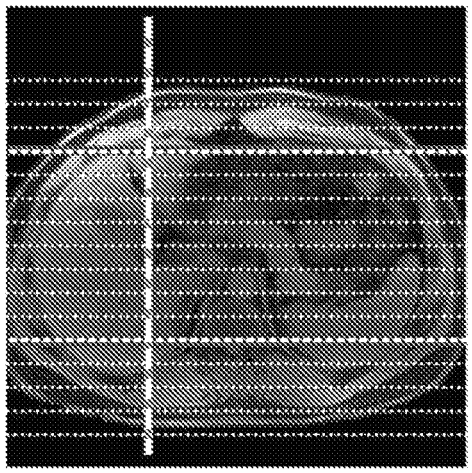
FIG. 1 shows an example of a one-plane (1PL) navigator 4D-SOPI acquisition scheme. Data from a sagittal navigator slice and two simultaneously excited coronal imaging slices are acquired within each TR in this example. The spacing between the coronal imaging slices is kept constant. The navigator slice is kept fixed, and the coronal slice prescription moves dynamically during a time series acquisition.
Figure 2:
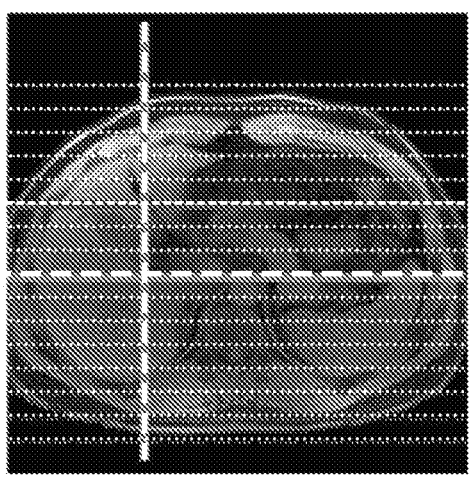
FIG. 2 shows an example of a two-plane (2PL) navigator 4D-SOPI acquisition scheme. Data from one sagittal navigator slice, one coronal navigator slice, and one coronal imaging slice are acquired within each TR. The sagittal and coronal navigator slices are kept fixed. The spacing between the simultaneously excited slices in the coronal plane varies depending on the location of the imaging slice.

Described here are systems and methods for providing image guidance for motion tracking and compensation in magnetic resonance imaging ("MRI") guided therapies, such as MRI-guided radiation therapies using an MR-linac or other MRI-guided radiation therapy system. In general, these systems and methods can include using simultaneous orthogonal plane imaging ("SOPI") to acquire images from a first slice that remains static throughout the acquisition, and from a plurality of slices that are orthogonal to the first slice. This first slice can be referred to in some instances as a "tracking" or "navigator" slice, and the plurality of slices that are orthogonal to the first slice can be referred to as "imaging" slices. An example of such a data acquisition scheme is shown in FIG. 1. In some embodiments, two static tracking slices can be used, where these two tracking slices are orthogonal to each other, and the imaging slices are parallel to the second tracking slice, as shown in FIG. 2. In other implementations, a plurality of parallel tracking slices can be used, where each tracking slice is then orthogonal to the imaging slices. In still other implementations, a plurality of both tracking and imaging slices can be used.

The series of images from the tracking slice (or multiple tracking slices) can be used to estimate motion of the subject that occurred during the data acquisition, and to track the position of targets (e.g., anatomical targets) during the delivery of radiation treatment. The estimated motion information can be used to gate the acquisition of data from the plurality of imaging slices, or to otherwise compensate images obtained from the imaging slices for the motion that occurred during their acquisition. Tracking the position of targets during the delivery of radiation treatment can be used to adjust, in real-time, the delivery protocol.

As one advantage, the methods described here can be used for tracking targets in real-time during a radiation, or other, treatment procedure. In these instances, the methods described in the present disclosure can be used to provide information that can be used to control the delivery of radiation, or other treatment, during such procedures. For instance, the series of images acquired from the tracking slice can be monitored to track the position of targets within the tracking slice while radiation, or other treatment, is being delivered. An example of treatments other than radiation treatment that can be monitored using the methods described in the present disclosure include ultrasound treatment (e.g., high-intensity focused ultrasound).

As one example, the tracking slice can be used to monitor the position of an organ-at-risk ("OAR") relative to the radiation field of an MR-linac or other MR-guided radiation treatment system. If the OAR is identified as moving into, or otherwise too close to, the radiation field, then that information can be used to control the radiation delivery. For instance, the radiation beam can be shut off when the OAR enters the radiation field, or otherwise moves into an undesirable position, on account of subject motion (e.g., respiration). A tracking slice can therefore be positioned such that movement of the OAR into the radiation field can be detected in the tracking slice.

As another example, the tracking slice can be used to monitor the position of a planned treatment volume ("PTV") relative to the radiation field of an MR-linac or other MR-guided radiation treatment system. If the PTV is identified as leaving the radiation field, then that information can be used to control the radiation delivery. For instance, the radiation beam can be shut off when the PTV leaves the radiation field on account of subject motion (e.g., respiration).

As another example, one tracking slice can be used to monitor the position of a surrogate organ (e.g., the lung-liver interface) for subsequent use in 4D-MRI reconstruction, while another tracking slice can be used to monitor the position of the PTV or OAR as described above.

As noted, multiple tracking slices can also be implemented, in which case more than one OAR can be tracked, more than one PTV can be tracked, or both an OAR and a PTV, or a surrogate organ (e.g., the lung-liver interface) and PTV or OAR can be tracked.

The methods described in the present disclosure also provide an advantage to measuring the truth-in-record for radiation delivered during a treatment fraction. A series of images obtained from the tracking slice can be used to estimate a motion signal indicating the motion of the subject that occurred during the acquisition of the imaging slices, and also during the delivery of radiation treatment to the volume from which the imaging slices were acquired. This motion signal can be used to compensate the imaging slices for motion-related errors, to bin the imaging slices into different motion bins (e.g., respiratory phase bins, cardiac phase bins), and so on. The motion signal can be based in the image domain (e.g., an intensity projection) or a frequency domain (e.g., by phase ramps according to the Fourier Shift Theorem).

As one example, the motion signal estimated from the series of images obtained from the tracking slice can be used to estimate motion parameters that can be applied to the images acquired from the imaging slices to compensate those images for motion-related errors. The compensated images can then be processed to compute an estimate of accumulated dose in the imaged volume.

As another example, the motion signal estimated from the series of images obtained from the tracking slice can be used to bin the images obtained from the imaging slices into different volumetric motion epochs that may span one or more motion phases (e.g., one or more respiratory or cardiac phases). For instance, the motion signal can be divided into different epochs and this information can be used when calculating the accumulated dose from the images acquired from the images slices. The time in different respiratory phases in different epochs can be used, for instance, to weight the accumulated dose calculated from images acquired during those time periods.

Using an accumulated dose computed from images acquired using the methods described in the present disclosure, an accurate assessment of the radiation delivered during a treatment procedure can be provided. The accumulated dose can be used, for instance, to identify spatial regions in the imaged volume that received higher radiation dose or lower radiation dose than prescribed in the treatment plan that was delivered. Using this information, the treatment plan for a subsequent treatment can be appropriately adjusted (e.g., by reducing dose to those regions that received higher than prescribed dose levels, by increasing dose to those regions that received lower than prescribed dose levels).

When implementing the methods described in the present disclosure, a SOPI pulse sequence can be used to simultaneously acquire data from one or more tracking slices and one or more imaging slices. In such acquisitions, the position of the one or more tracking slices remains the same during subsequent repetition time ("TR") periods, whereas the position of the one or more imaging slices changes in subsequent TR periods. When data are acquired from more than one imaging slice in a given TR period, a multiband radio frequency ("RF") pulse can be used to simultaneously excite spins in those multiple different imaging slices.

As noted above, the tracking slice is orthogonal to the imaging slices; although, in some embodiments a second tracking slice that is orthogonal to the first tracking slice and parallel with the imaging slices can also be used. In those instances where a second tracking slice is used, a multiband RF pulse can be used to simultaneously excite spins in the second tracking slice and one or more imaging slice. In some other embodiments, the second tracking slice can be parallel with the first tracking slice. It will be appreciated that any suitable combination of a plurality of tracking slices can be implemented, where the position of those tracking slices will remain constant in subsequent repetition time periods, whereas the position of the imaging slices will change in subsequent repetition time periods.

In some embodiments, the position of a tracking slice can be adjusted based on feedback from the images acquired in the tracking slice, the imaging slices, or both. For instance, it may be determined during imaging that the tracking slice location does not provide the best information for the particular subject being imaged. This may be the situation if the subject moves during imaging, if the subject's respiration pattern changes significantly during imaging or radiation treatment, or for other reasons. In these instances, the position of a tracking slice can be updated to a different position where the tracking slice will remain stationary.

SOPI can include any number of pulse sequences that are adapted to simultaneously acquire data from two orthogonal slices. Such implementations allow for rapidly and simultaneously imaging a moving target in two orthogonal planes. Using this imaging technique, more spatial information about the object being imaged can be obtained in a single acquisition, motion of the underlying object can be captured in a plane along all three orthogonal directions, and images that are free of intra-slice motion artifacts can be reconstructed. The improved visualization of the target and nearby structures can also be used to aid in the monitoring of intrafraction motion, to improve the accuracy of dose delivery, and to compute dose accumulated during a radiation treatment.

Anticipating and measuring respiratory motion during a fraction of radiation therapy is crucial to deposit the intended dose. SOPI can aid in the measurement of these motions in real time and improve the accuracy of radiation delivery by eliminating interslice motion seen in interleaved orthogonal plane cine acquisitions.

Motion prediction algorithms used for gating and tracking benefit from extremely low latency information. While the SOPI images are acquired at a reasonable frame rate, a high temporal resolution motion surrogate inherent to the MRI sequence can be advantageous for some applications. The use of pseudo-projection navigation can be implemented with the SOPI sequence to provide motion surrogate signals. In this technique, phase encoding lines within a predefined region near the center of k-space are filtered and used to generate a 1D projection of the moving anatomy.

It is an aspect of the present disclosure to provide methods for simultaneously enabling real-time motion monitoring and truth-in-delivery analysis for integrated MR-guided radiation therapy systems.

As described above, a SOPI acquisition can be adapted to permit dynamic updating of slice positions in one plane (e.g., via the imaging slices) while keeping the other plane position fixed (e.g., via the tracking slice). In this implementation, cine images from the static plane can be used for motion monitoring and as image navigators to sort stepped images in the other plane, thereby producing dynamic 4D image volumes for use in dose accumulation.

Unique 4D-MRI epochs can also be reconstructed from a time series of images.

Dose from a region can be calculated on each 4D respiratory phase bin and epoch image, scaled by the time spent in each bin, and then rigidly, deformably, or otherwise, accumulated using MIM Maestro® (MIM Software, Inc.; Cleveland, Ohio) or another suitable dose accumulation algorithm implemented with a hardware processor and memory. For instance, a treatment planning system ("TPS") can be used to calculate the dose. As one example, the TPS can be a Monaco® TPS (Elekta Instrument AB; Stockholm, Sweden). In some implementations, the TPS can be configured to incorporate the magnetic field generated by the MR-linac, which may be a 1.5 T field in some instances.

Following irradiation, actual dose deposited in the volume (e.g., to the subject in the volume) can be determined. As one example, the methods described in the present disclosure were tested using radiosensitive and MR-visible gels. The actual dose deposited in these gels can be estimated by applying an $R_1$ versus dose calibration curve to $R_1$ maps obtained from the imaging slices.

Figure 3:
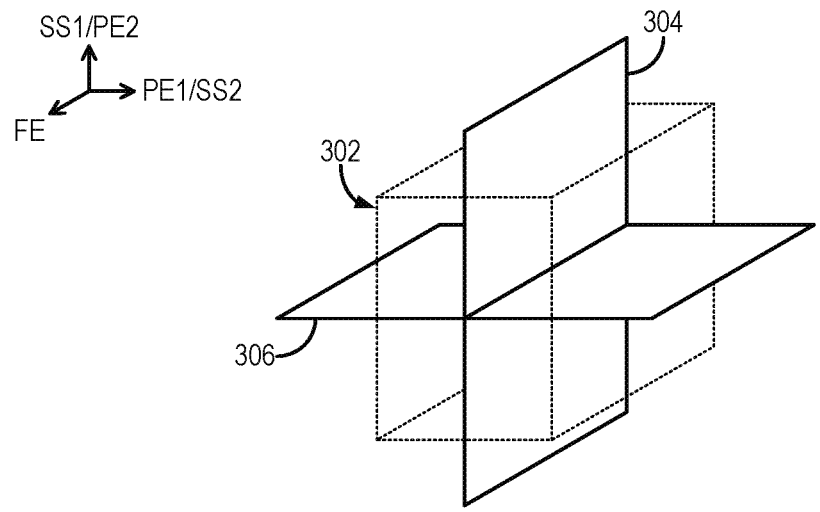
FIG. 3 illustrates an example simultaneous orthogonal plane imaging ("SOPI") acquisition scheme, in which data are acquired from two orthogonal slices in a single acquisition.

An example of a SOPI acquisition scheme is shown in FIG. 3, where an object 302 is simultaneously imaged in two orthogonal slices 304, 306. In this example, the first slice 304 is spatially encoded using slice encoding along the z-direction, phase encoding along the y-direction, and frequency encoding along the x-direction. The second slice 306 is then spatially encoded using slice encoding along the y-direction, phase encoding along the z-direction, and frequency encoding along the x-direction. It will be appreciated that the directions associated with the slice, phase, and frequency encodings in this example are selected for illustrative purposes, and that the various encoding directions can be aligned any three arbitrary orthogonal directions. The directions can thus be more generally referred to as the first slice encoding direction (SS1), which is also the second phase encoding direction (PE2); the first phase encoding direction (PE1), which is also the second slice encoding direction (SS2); and the frequency encoding direction (FE).

As an example, the first slice 304 can correspond to a tracking slice and the second slice 306 can correspond to an imaging slice, as described above. In this example, the position of the first slice 304 would not be changed from one TR period to the next, while the position of the second slice 306 would be changed in subsequent TR periods. For instance, the second slice 306 could be moved to different slice planes along the first slice encoding direction (SS1).

Figure 4:
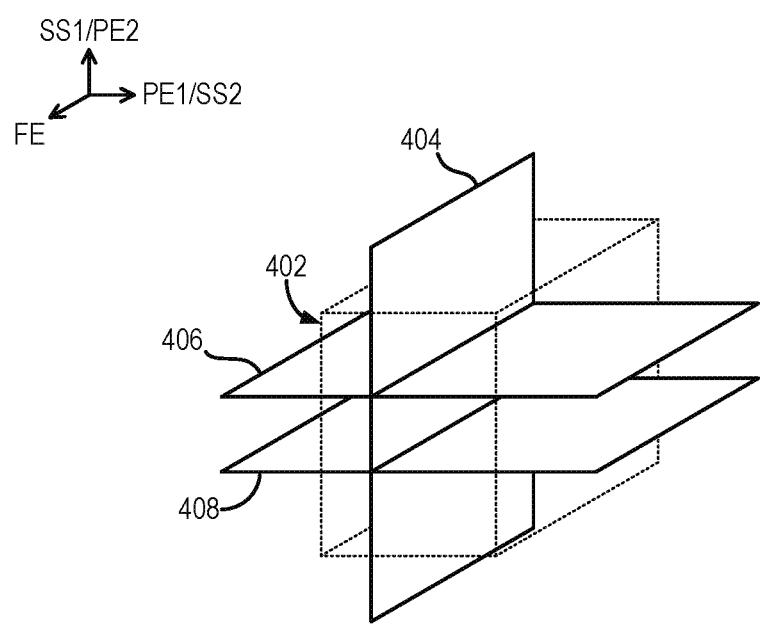
FIG. 4 illustrates an example multiplexed SOPI ("mSOPI") acquisition scheme, in which data are simultaneously acquired from one slice along a first axis and from multiple slices along a second axis that is orthogonal to the first axis, in a single acquisition.

In general, a SOPI pulse sequence can be adapted for simultaneous multislice imaging by replacing single-band RF pulses with multiband RF pulses to simultaneously excite more than one slice on each orthogonal axis. Such implementations of SOPI may be referred to as multiplexed SOPI (mSOPI). An example of a multiplexed SOPI acquisition scheme is shown in FIG. 4, where an object 402 is simultaneously imaged in a first slice 404, and in a second slice 406 and a third slice 408 that is parallel to the second slice 406. Both the second slice 406 and the third slice 408 are orthogonal to the first slice 404. Although the example in FIG. 4 illustrates two slices being simultaneously excited along a given orthogonal axis (i.e., SS1 or SS2), it will be appreciated that with the appropriate multiband RF pulse, more than two slices can be excited along a given orthogonal axis.

In the example shown in FIG. 4, the first slice 404 is spatially encoded using slice encoding along a first slice encoding axis, SS1; using phase encoding along a first phase encoding axis, PE1; and using frequency encoding along a frequency encoding axis, FE. The second slice 406 and the third slice 408 are spatially encoded using slice encoding along a second slice encoding axis, SS2, which is the same as the first phase encoding axis, PE1; using phase encoding along a second phase encoding axis, PE2, which is the same as the first slice encoding axis, SS1; and using frequency encoding along the same frequency encoding axis, FE, as the first slice 404.

As an example, the first slice 404 can correspond to a tracking slice and the second slice 406 and third slice 408 can correspond to imaging slices, as described above. In this example, the position of the first slice 404 would not be changed from one TR period to the next, while the position of the second slice 406 and third slice 408 would be changed in subsequent TR periods. For instance, the second slice 406 and third slice 408 could be moved to different slice planes along the first slice encoding direction (SS1).

As another example, the first slice 404 and second slice 406 can correspond to tracking slices and the third slice 408 can correspond to an imaging slice, as described above. In this example, the position of the first slice 404 and the second slice 406 would not be changed from one TR period to the next, while the position of the third slice 408 would be changed in subsequent TR periods. For instance, the third slice 408 could be moved to different slice planes along the first slice encoding direction (SS1).

The SOPI pulse sequences described in the present disclosure acquire images in two orthogonal imaging planes; however, the sequences can also be adapted to acquire images in a third orthogonal imaging plane. In these instances, a separate readout gradient would be applied along the slice select axis of one of the other two orthogonal slice groups. Thus, as one example, the spatial encoding for the first and second orthogonal imaging planes would be as described above, but spatial encoding for the third orthogonal imaging plane would be implemented using slice encoding along the frequency encoding direction (FE) with phase encoding along either the SS1/PE2 or SS2/PE1 direction, and frequency encoding then along either the SS2/PE1 or SS1/PE2 direction.

Described above are two different variations of a 4D-SOPI pulse sequence that can be implemented in accordance with the methods described in the present disclosure. The use of a simultaneous multislice ("SMS") factor of two was used in the imaging slice groups described above (i.e., two imaging slices were described as being simultaneously excited). In other embodiments, however, different SMS factors can also be implemented. The first variant, shown in FIG. 1, can be referred to as a one-plane (1PL-4D-SOPI) implementation that acquires a cine tracking (or navigator) slice in one orthogonal plane while stepping through groups of SMS imaging slices in the second orthogonal slice plane. The two-plane variation (2PL-4D-SOPI), shown in FIG. 2, acquires one cine tracking (or navigator) slice in each of the orthogonal planes while acquiring a single imaging slice at a time.

An example SOPI pulse sequence is provided below. Expressions for the zeroth gradient moments of the lobes shown in these examples are also derived. Although the pulse sequences described below implement Cartesian sampling of k-space, SOPI pulse sequences can also be adapted for radial or spiral readout trajectories to provide additional robustness to intraslice motion artifacts.

Figure 5:
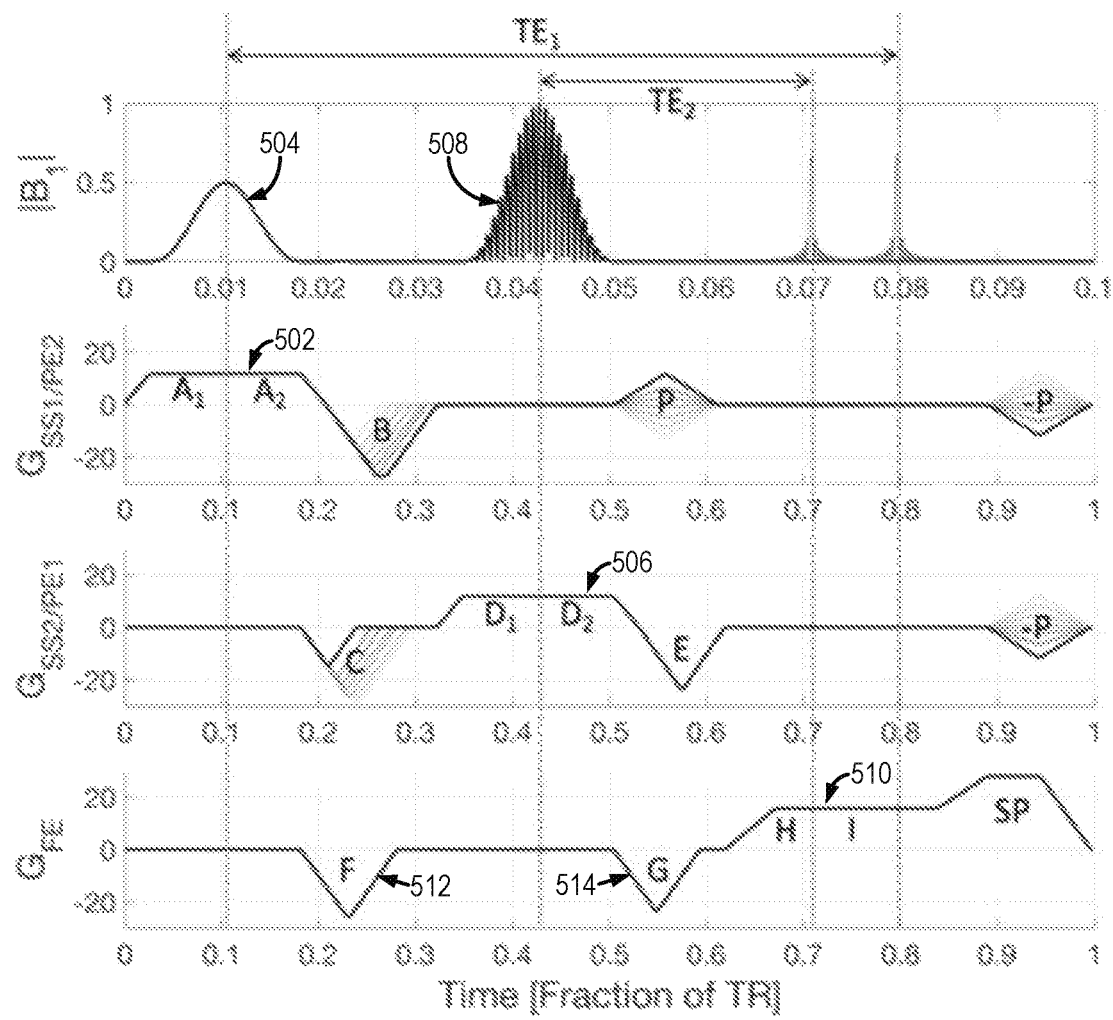
FIG. 5 is an example of a simultaneous orthogonal plane imaging ("SOPI") pulse sequence with non-equal echo times ("nETE"). In this example, the orthogonal slice packets are acquired with non-equal echo times and are separated via a simultaneous image refocusing (SIR) readout. The areas of the B and C gradient lobes are dependent on the current phase encoding moment, P. The phase encoding axis of one orthogonal slice group is on the slice select axis of the other orthogonal slice group. The two slice groups are frequency encoded on a common axis. A single-band RF pulse is played out to excite a slice in the navigator plane while a multiband RF pulse is used to excite slices in the (orthogonal) imaging plane.

One example SOPI pulse sequence described in the present disclosure is a non-equal echo time (nETE) spoiled gradient (SPGR) SOPI pulse sequence. A pulse sequence diagram for this example implementation is shown in FIG. 5. In this pulse sequence, slices are sequentially excited on orthogonal axes. Each slice is phase encoded along the slice select axis of the other slice. An extended readout gradient refocuses separate gradient echoes for each slice in the reverse of the order in which they were excited, which results in unequal echo times between the slices. Phase rewinder and readout spoiler gradients can be played after the readout plateau ends. In some embodiments, In the pulse sequence shown in FIG. 5, gradient moments A1 and A2 are defined to be the gradient lobe areas (including ramps) of the first slice selection gradient 502 separated by the isocenter of the first RF pulse 504. Gradient lobes D1 and D2, likewise, are the gradient lobe areas of the second slice select gradient 506 separated by the isocenter of the second RF pulse 508. For simplicity, both orthogonal slices are to be phase encoded with the same gradient moment of P, though different phase encoding lines for both slices can be sampled within the same repetition time (TR) period. The gradient moment of gradient lobes B and C are dependent on the current k-space line.

As shown in FIG. 5, the first RF pulse 504 is a single band RF pulse and the second RF pulse 508 is a multiband RF pulse. The first RF pulse 504 in this implementation to excite spins in a single slice location, such as a tracking slice location. The second RF pulse 508 in this implementation is used to simultaneously excite spins in multiple different slice locations, which may be multiple different parallel imaging slices, or a second tracking slice in addition to one or more parallel imaging slices.

As one example, the second RF pulse 508 can be implemented as phase-tagged RF pulses, such as phase-tagged sinc pulses. Phase tags can be used to apply CAIPIRINHA phase ramps to achieve a FOV/2 shift between simultaneously excited slices within the 4D imaging plane. Additionally, the SMS slices can be excited in quadrature to avoid interference and to facilitate a phase constrained reconstruction. To accelerate the acquisition of each frame, an in-plane reduction and partial Fourier acquisition can also be used.

The net gradient-induced phase accumulation of the first slice along the SS1/PE2 axis should be zero by the beginning of the readout gradient 510. Given that the second slice also must have accumulated a gradient moment of P by the beginning of the readout gradient 510, the following expression can be given for the zeroth gradient moment in gradient lobe B:

$$B = -A_2 - P \qquad (1).$$

The phase accumulated in the second slice after the second RF pulse isocenter should be rewound prior to readout. Therefore:

$$E = -D_2 \qquad (2).$$

Also, the moment of the first slice along the SS2/PE1 axis should be the phase encoding moment, P, before the beginning of the readout. With this constraint, the zeroth gradient moment in gradient lobe C can be expressed as follows:

$$C = -D_1 + P \qquad (3).$$

With a simultaneous image refocusing (SIR) readout, the gradient echo signals S1 and S2 are acquired at non-overlapping portions of the readout gradient 510, which has an amplitude calculated based on the bandwidth and field-of-view (FOV). The aliased signals from the SMS slices remain entangled within the gradient echo corresponding to the 4D imaging slice packet. The SOPI sequence with a SIR readout is fastest when the gradient echo for the second slice occurs before that of the first slice. The following prephaser gradient moments are used for this type of readout.

$$F_{nETE} = -I \qquad (4);$$

$$G_{nETE} = -H \qquad (5).$$

With these frequency encoding prephaser gradients (512, 514), the echo time between the two slices is not equal. If an even faster acquisition is desired, the gradient echoes from the orthogonal slices may be acquired in an aliased (e.g., in which the echoes are combined) manner during the same portion of a non-extended readout gradient. In this case, only the prephaser gradient lobe 514 after the second excitation 508 needs to be applied, resulting in the following gradient lobe areas:

$$F_{nETE,Aliased} = 0 \qquad (6);$$

$$G_{nETE,Aliased} = -H \qquad (7);$$

$$I_{nETE,Aliased} = 0 \qquad (8).$$

In a SOPI pulse sequence with a readout that results in aliasing as described above, the orthogonal slices will be superimposed in the reconstructed image. While coil sensitivity differences of overlapping voxels of orthogonal slices should be significantly greater than those in overlapping pixels of parallel slices, image quality can still be improved by applying a CAIPIRINHA RF phase cycling pattern that shifts one of the slices relative to the other within the FOV to reduce the number of superimposed voxels.

In some implementations of the nETE SOPI acquisitions, the flip angle of the two RF pulses can be adjusted so the orthogonal images (with different echo times) have more similar contrast to noise ratio for a given TR.

The order in which orthogonal slice groups are excited when using an nETE SOPI acquisition can be swapped from one repetition to the next. In these implementations, the echo time of each orthogonal slice group will change between repetitions.

In some embodiments, the free induction signal pathway can be crushed for both orthogonal slices, or slice groups, by applying a crusher gradient along the readout axis before the readout gradient is applied.

In some implementations, the frequency encoding prephaser gradients (F and G) and the readout bandwidth can be adjusted to ensure that the gradient echo for each slice plane occurs in the order in which they were excited and with the same echo time. This equal echo time ("ETE") implementation may be designed by adjusting the prephaser amplitudes and the readout bandwidth such that the time between gradient echoes is equal to the time between the isocenters of the RF pulses (ATRF):

$$F_{ETE} = I; \quad (9)$$

$$G_{ETE} = -H - I; \quad (10)$$

$$bw_{ETE} = \frac{N}{\Delta T_{RF}}; \quad (11)$$

where N is the number of pixels in the frequency encoding direction. With these parameters, the orthogonal slices are rephased in the order in which they were excited, and the adjusted bandwidth assures that the echo time of each slice is identical. The phase encoding and slice select rewinding gradients remain unchanged from the nETE SPGR SOPI sequence.

In spoiled gradient recalled echo sequences (e.g., SPGR, FLASH), phase rewinding gradient lobes are played immediately after the readout. In the SPGR SOPI sequences, these gradients (–P) are played on the SS1/PE2 and SS2/PE1 axes. A spoiler gradient (SP) with the same polarity of the readout gradient is also played concurrently.

The regions where slices intersect each other inside the target can lead to saturation regions running along the frequency encoding direction representing the slice profile of the corresponding orthogonal slice. If a smaller region of saturated signal is desired (e.g., for smaller targets like the pancreas), the tradeoff is acquisition speed. To excite a thinner slice, a larger gradient amplitude is needed, and thus a larger slice rewinder gradient is also needed. This effectively increases the duration of time between the two RF pulses and stretches the minimum achievable TE and TR.

Fat suppression can be implemented in the SOPI pulse sequences described in the present disclosure. This fat suppression can further improve image contrast and target delineation.

The SOPI pulse sequences described in the present disclosure can also be adapted to implement RF pulses with a short duration and extremely low bandwidth that still maintain good slice profiles. This implementation would decrease the time between the two RF pulses, leading to a shorter minimum TE and TR, and to higher frame rates.

Although the example described above implements an SPGR pulse sequence, it will be appreciated by those skilled in the art that other pulse sequences can be adapted and implemented for a SOPI acquisition. For example, a reversed fast imaging in steady-state precession (reversed FISP, or PSIF) pulse sequence can also be implemented. Like the SPGR pulse sequence described above, in a PSIF pulse sequence adapted for SOPI, slices are sequentially exited on orthogonal axes, and each slice is phase encoded along the slice select axis of the other slice.

In general, a SOPI pulse sequence can be adapted for simultaneous multislice imaging by replacing single-band RF pulses with multiband RF pulses to simultaneously excite more than one slice on each orthogonal axis. Such implementations of SOPI may be referred to as multiplexed SOPI (mSOPI). By exploiting variations in coil sensitivity profiles, the aliased parallel slices along each orthogonal axis may be separated. CAIPIRINHA phase modulations of at least one slice on each orthogonal axis may be used to improve the separation of the slices.

For example, in CAIPIRINHA acquisitions, RF phase ramps are applied along the phase encode (PE) direction with slope $m_{CAIPI}$ (defined here with units of radians per PE line) and intercept $b_{CAIPI}$. In an example mSOPI pulse sequence, one slice on each orthogonal axis can be selected with $m_{CAIPI}=0$ rad/PE and $b_{CAIPI}=0$ rad. The second slice on each orthogonal axis can then be shifted by a percentage of the field-of-view, such as one-half the field-of-view (i.e., FOV/2), and acquired in quadrature relative to the first slice with $m_{CAIPI}=\pi$ rad/PE and $b_{CAIPI}=\pi/2$ rad. In consecutive repetitions, $b_{CAIPI}$ on the shifted slice can be incremented by $\pi$ radians (i.e., $b_{CAIPI}$ on the shifted slice alternated as +π/2, –π/2, +π/2, . . . ).

When the SOPI pulse sequence is used for imaging moving anatomy, it may not be sufficient to use a single reference scan to obtain calibration data to separate aliased slices. In such instances, an autocalibrating acquisition and phase-constrained 2D-SENSE-GRAPA reconstruction process can be implemented for mSOPI.

To reconstruct the tracking (or navigator) images from an orthogonal tracking slice, a conventional image reconstruction can be implemented. For instance, if the data acquired from the tracking slice are fully sampled, a conventional Fourier transform based reconstruction can be used. When in-plane acceleration is used in the tracking slice, a parallel imaging reconstruction can be used. As one example, a GRAPPA interpolation kernel can be calculated from fully sampled autocalibrating signal ("ACS") lines near the center of k-space. This kernel can be used to interpolate the skipped phase encoding lines. When partial Fourier sampling is also used, a homodyne partial Fourier algorithm can be used to restore the conjugate symmetric portion of k-space.

A phase constrained 2D-SENSE-GRAPPA algorithm can be used to separate signals from simultaneously excited slices in the 4D imaging slice group. This kernel can be calculated from a low resolution calibration scan. The kernel is applied to the undersampled portions of the k-space of an extended readout FOV representation of the SMS slices. A virtual conjugate coil ("VCC") method can be used to exploit the phase differences between the SMS slices. The same homodyne reconstruction algorithm can be used to restore the conjugate symmetric portion of k-space of each SMS slice when partial Fourier sampling is used. An example of such an algorithm is described below.

When multiple parallel tracking slices are implemented, a phase constrained, or other suitable SMS, reconstruction can be used to separate signals from the simultaneously excited tracking slices.

Figure 6:
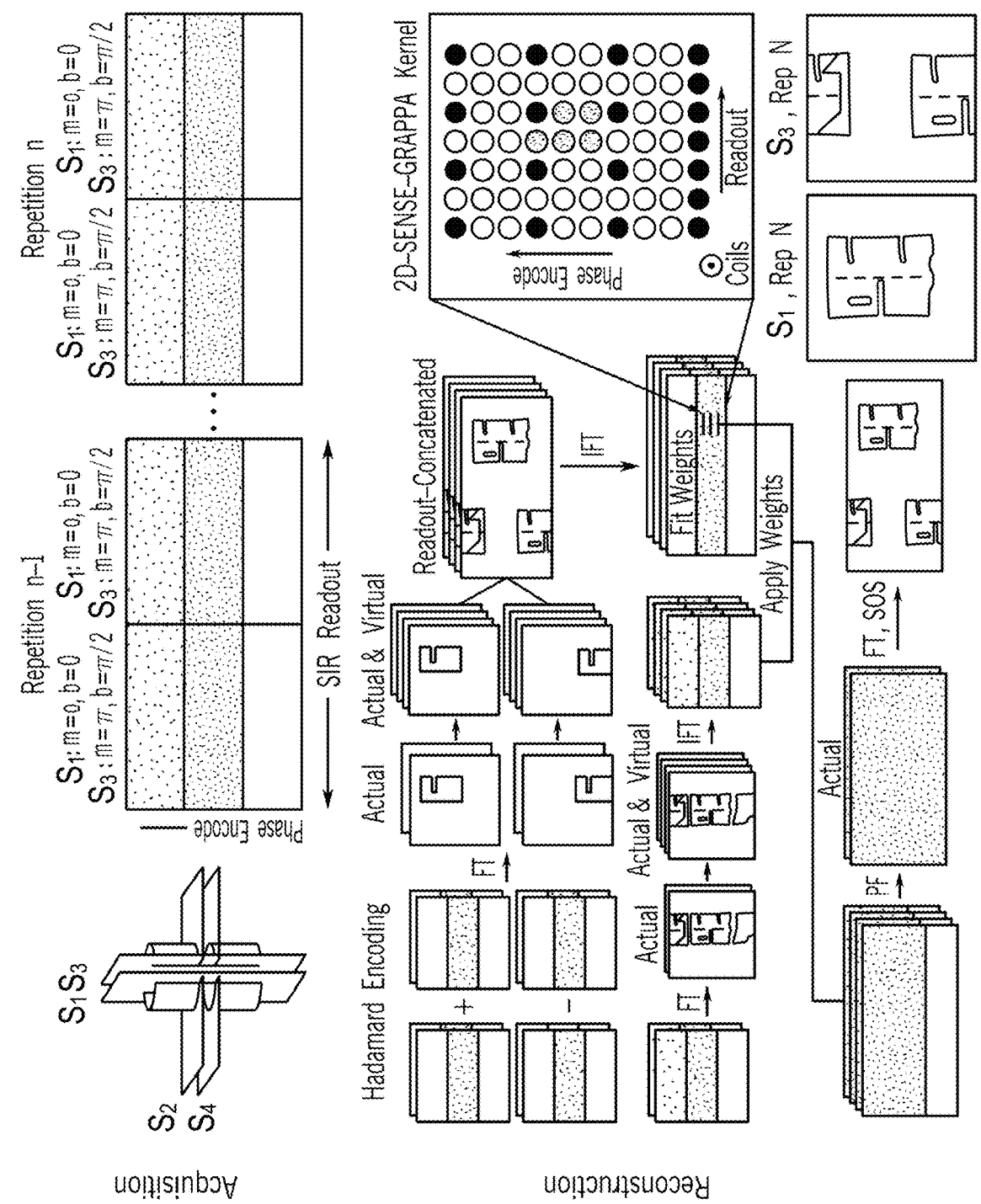
FIG. 6 is a flow diagram setting forth the steps of an example method for acquiring data using a multiplexed SOPI acquisition and reconstructing images from that acquired data.

Referring now to FIG. 6, a flow diagram is illustrated as setting forth the steps of an example method for acquiring data using a multiplexed SOPI pulse sequence and for reconstructing images from such data.

Data are acquired from a subject using a multiplexed SOPI acquisition. As an example, the data can be acquired using multiplexed SOPI acquisition such as the one described above. Additional acceleration techniques can also be implemented, such as by using partial Fourier (PF) encoding an in-plane acceleration (e.g., by skipping phase encoding lines). Using the acquisition described above, an RF phase ramp will shift one slice along each axis within the FOV. The intercept of this phase ramp, $b_{CAIPI}$, can be incremented by $\pi$ radians in consecutive repetitions. The fully sampled region in the center of k-space from consecutive repetitions can then be added and subtracted to obtain reference data for each slice. As an example, Hadamard encoding can be used to separate the k-space data acquired for the parallel slices on each orthogonal axis.

When the pair of slices in each orthogonal slice packet are excited in quadrature, the reference data for each slice separated from Hadamard encoding can be used to compute phase-constrained 2D-SENSE-GRAPPA weights to separate the aliased slices from a single repetition. For instance, virtual coil reference images can be created by taking the complex conjugate of the images from only the fully-sampled region of the Hadamard separated k-spaces for each orthogonal slice group. The virtual coil reference images are appended to the actual coil images.

The reference images are concatenated along the readout direction, brought to k-space, and a 2D-SENSE-GRAPPA kernel (e.g., a 4×4 2D-SENSE-GRAPPA kernel) is fit to simultaneously unalias a single repetition in the slice and in-plane directions. In the example kernel geometry shown in FIG. 6, closed black circles are source points, the grayed out points are target points, and the open circles represent unacquired points.

The resulting weights can be applied to the aliased data from a single repetition (actual and virtual coils), filling in missing points in the undersampled phase and frequency encoding directions. To account for partial Fourier sampling, the phase encoding lines still missing after 2D-SENSE-GRAPPA in the actual coils can be filled in by enforcing conjugate symmetry in k-space after a background phase correction. An inverse Fourier transform and sum of squares coil combination can then be used to produce an unaliased image. The individual slices were obtained by segmenting the readout-extended FOV image. This process is repeated to separate slices S2 and S4.

In the non-limiting example described above, a SIR readout can be used to separate the orthogonal slice packets, and an autocalibrating phase-constrained 2D-SENSE-GRAPPA reconstruction can be used to separate the overlapped parallel slices along each axis. The mSOPI sequence enables improving slice coverage while keeping the frame rate as high as it is for non-multiplexed SOPI. The partial Fourier acquisition can allow for a larger fully sampled ACS region near the center of k-space to be sampled for a given frame rate.

The SOPI pulse sequences described above implement a T1-weighted contrast with an SPGR acquisition. In other embodiments, however, pulse sequences that acquire data with contrast weightings different than T1-weighting can also be acquired using SOPI, at least in part. As one example, a balanced steady state free precession ("bSSFP") sequence with mixed T2/T1 can be implemented.

When an object is moving during data acquisition there will be spatiotemporal correlations in the acquired k-space data. These correlations can be exploited using k-t GRAPPA to interpolate the undersampled k-t space of alternating, orthogonal slice non-T1-weighted acquisitions. In k-t GRAPPA, the signal for a coil, j, and time point, t, can be described as a linear combination of signals from $N_k$ neighboring k-space locations, $N_t$ neighboring time frames, and all $N_c$ receiver coils:

$$S_j(k, t) = \sum_{i_c=1}^{N_c} \sum_{i_k=1}^{N_k} \sum_{i_t=1}^{N_t} S_{i_c}[k(i_k), t(i_t)] \cdot n_j^{i_c, i_k, i_t}; \quad (12)$$

Because the k-t correlations are independent of image contrast, the k-t GRAPPA weights may be calculated from fully-sampled T1-weighted SOPI data and applied to the undersampled non-T1-weighted images. Furthermore, even when a Cartesian SOPI calibration acquisition is employed, the alternating non-T1-weighted scan may be performed with an arbitrary k-space trajectory.

The continuously adapting treatment cycle afforded by MR-guided radiation therapy ("MR-gRT") systems allows radiation treatment replanning with every measurement of anatomy. Advantageously, the replanning could be done in real-time during a treatment fraction. Alternatively, the replanning may also be done between fractions.

If a full 3D volume of the anatomy is known at every point during a treatment fraction, then the dose that was actually deposited in that fraction can be calculated, accumulated, and used to adaptively replan the next fraction. The 3D volumetric estimates should be obtained at a very high temporal resolution.

As described above, images can be sorted based on the motion information derived from the series of tracking images. For instance, the normalized cross correlation coefficient between each incoming tracking image and the first frame can be used to estimate a motion surrogate signal. For each desired 4D-MRI epoch, the motion surrogate can be placed into one of a number of different respiratory bins (e.g., six different respiratory bins) based on the signal amplitude. The imaging slices acquired concurrently with each frame of the tracking slice can be placed into the corresponding respiratory phase. Repeat images within each bin can be averaged.

Figure 7:
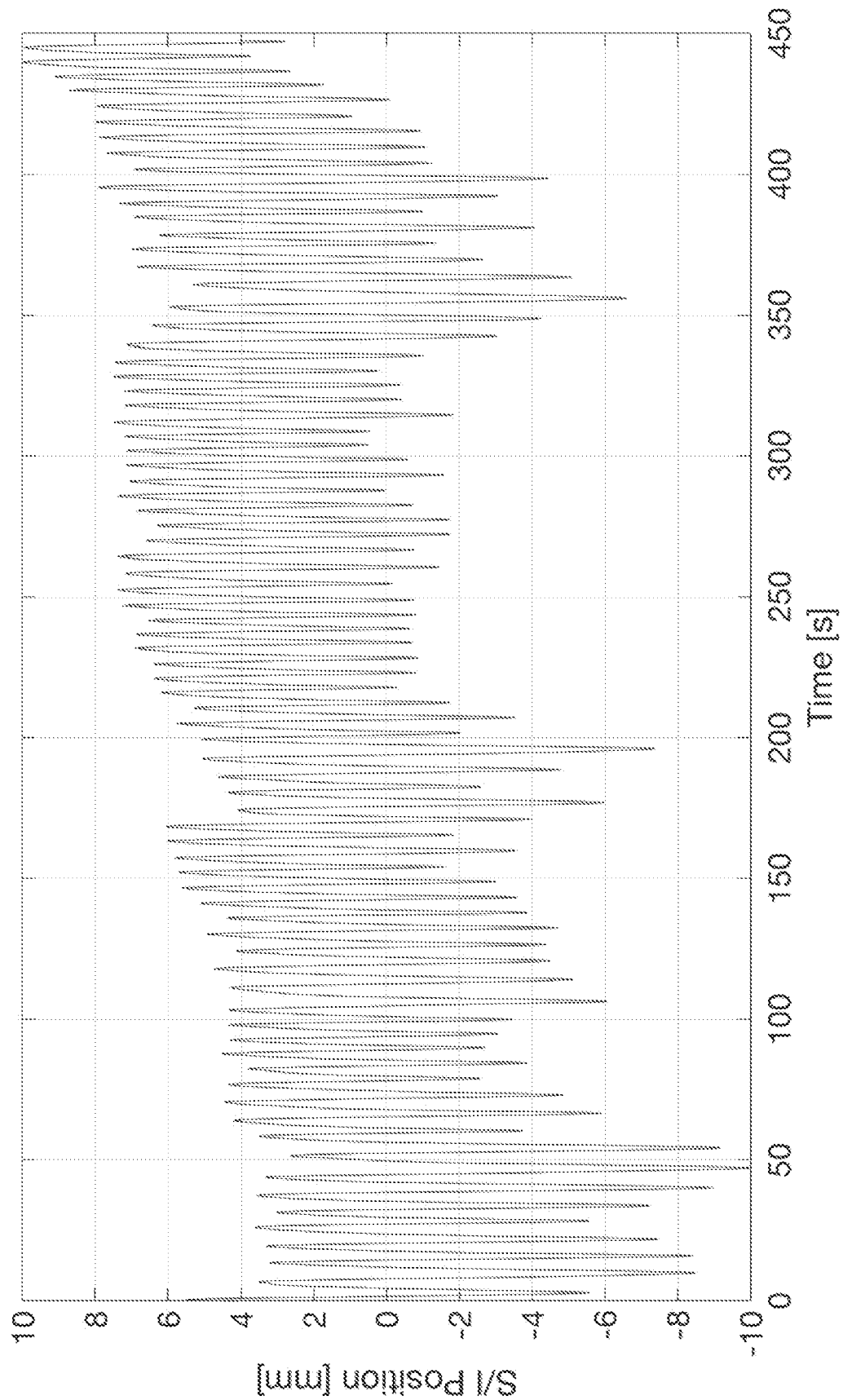
FIG. 7 is an example of a respiratory waveform used to drive dynamic motion phantom in an example study. A waveform with breathing irregularities was selected to demonstrate the necessity to collect serial 4D-MR images during the treatment fraction.

In an example study, a patient waveform extracted from a Varian RPM system during a 4D-CT scan of a pancreas patient was acquired, and is shown in FIG. 7. This waveform was used to drive the target of an MR-compatible dynamic motion phantom (Model 008M, CIRS, Norfolk, MA) in the superior-inferior direction. Data from a 1PL-4D-SOPI FISP scan were acquired with a single sagittal navigator slice and 62 coronal slices with a thickness of 3 mm. The TE1/TE2/TR from the scan were 3.5/1.5/5.3 ms, respectively. A flip angle of 20 degrees was prescribed. The FOV and matrix size were 340 mm and 128×128. A reduction factor of three (R=3) and ⅝ partial Fourier were used for in-plane acceleration. With 48 phase encode lines per frame, the total amount of time to acquire k-space data for an SMS=2 pair of coronal slices and sagittal navigator slice was approximately 0.25 seconds. Three 4D-MRI epochs with 5 bins were reconstructed, each using a sequential ⅓ of the data. A brief, low-resolution single-band calibration scan was performed to calibrate the 2D-SENSE-GRAPPA interpolation kernels.

In another example study, identical timing and resolution parameters used in the phantom experiment were used to acquire 1PL-4D-SOPI FISP data in the abdomen of a consenting healthy volunteer. Four 4D-MRI epochs of 4 bins were reconstructed for this scan. Additionally, a brief 2PL-4D-SOPI scan was acquired, and a single volume was reconstructed. The same calibration scan as in the phantom experiment was performed prior to acquisition of the 4D-MRI.

An dose accumulation experiment simulating a hypofractionated pancreas cancer MR-gRT fraction was also performed. A 3D-printed structure was fabricated to model the pancreas and immediately adjacent duodenum OAR. An air-filled cavity within the "duodenum" was incorporated to simulate an air pocket within the intestine. Due to the electron return effect, it was expected that localized dose increases would occur at the interface of the duodenal wall/air cavity.

Fifteen reconstructed 3D volumes obtained from the 1PL-4D-SOPI acquisition described above (5 bins per 4D epoch; 3 total 4D epochs) were resampled to 1 mm cubic voxels and then loaded into a research version of the Monaco treatment planning system (TPS) (v5.12.02, Elekta Instruments AB, Stockholm, Sweden). Electron densities of each phantom structure were determined from a CT scan of the phantom (Definition AS, Siemens Healthcare, Erlangen, Germany) and assigned in Monaco. For each of the fifteen volumes, dose resulting from a single 4 cm×15 cm open field oriented at gantry=0 degrees was calculated using a 2 mm grid spacing and 1% statistical uncertainty per control point. The effects of the cryostat and presence of the transverse 1.5 T magnetic field were incorporated during dose calculation. During this process, the position of the beam was kept fixed relative to the static components of the phantom (i.e., the phantom target was at different positions relative to the treatment field depending on 4D bin and epoch number). The patient respiratory waveform shown in FIG. 7 was 7.5 minutes in duration. At a dose rate of 432 MU/minute on the MR-Linac (Unity, Elekta Instruments AB), approximately 3200 MU were required for continuous irradiation over a 7.5-minute period. The relative monitor units (MU) used for dose calculation of each bin and epoch was determined based on the navigator waveform analysis from FIG. 7. The Monaco TPS calibration was set to deliver 1 cGy/MU to water at a 10 cm depth and 143.5 cm source-to-axis distance. However, the absolute calibration of the MR-Linac at the same position was measured to be 0.8766 cGy/MU at the time of the experiment. Therefore, the doses for each bin and epoch were scaled by 0.8766 to account for the difference between planned and actual absolute dose.

The scaled doses from all fifteen treatment plans was then sent to MIM (v6.7.6, MIM Software, Cleveland, OH). Local rigid registration was performed to align the targets for each 4D bin and epoch to a chosen reference target position of bin 5, epoch 3. After registration, doses were consecutively summed to produce an accumulated dose.

The dynamic motion phantom was then positioned on the MR-Linac. The pancreas and duodenum structures of the 3D printed target were filled with rFOX radiosensitive gel. The phantom motion was driven with the identical motion waveform used for the 1PL-4D-SOPI acquisition and simultaneously treated using a static 4 cm×15 cm field with 3200 MU.

Following irradiation, quantitative T1 mapping of the dynamic motion phantom and target was performed using DESPOT1 with five flip angles (3, 6, 10, 20, 30 degrees) and TR=20 msec. The 3D T1 map was converted to absolute dose by applying a calibration curve obtained from preliminary measurement of ten tubes exposed to known radiation doses ranging from 0 to 4000 cGy. The 3D absolute dose was compared against the accumulated dose from MIM using dose differences. In addition, dose-volume histogram metrics for individual evaluation ring contours around the pancreas and duodenum were compared.

Figure 8A:
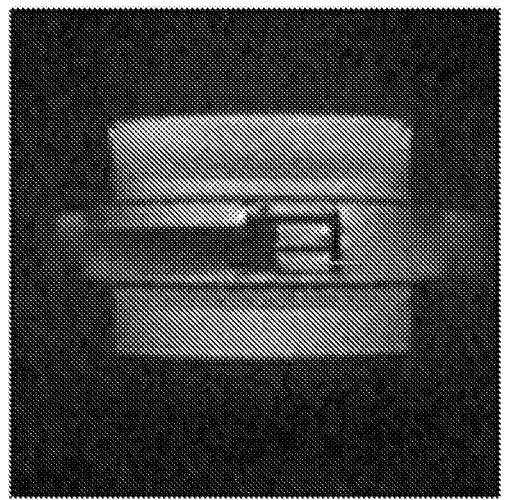
FIG. 8A is an example tracking, or navigator, image.
Figure 8B:
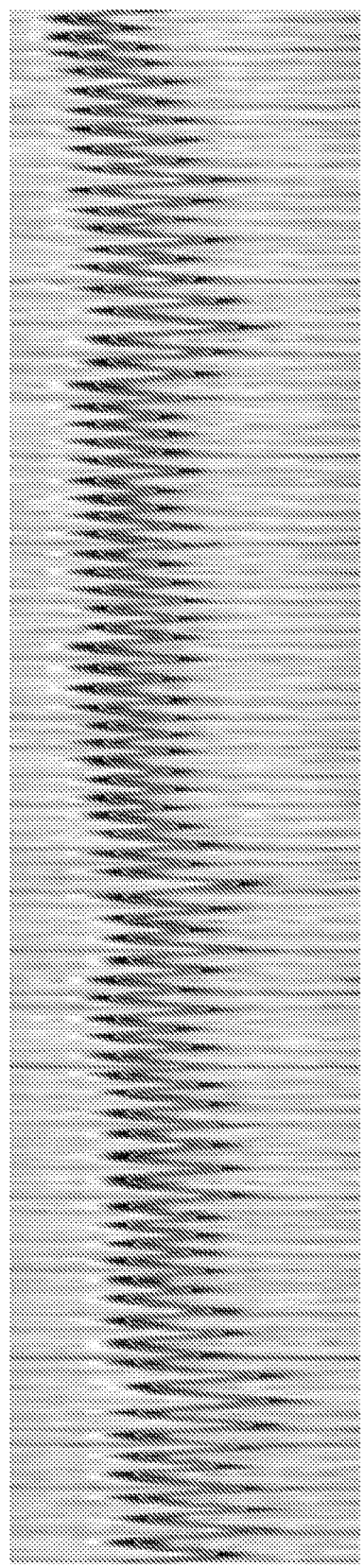
FIG. 8B is the respiratory motion waveform extracted from an intensity projection through the wall of the moving target in the example tracking image of FIG. 8A.

An example sagittal navigator image from the phantom experiment is shown in FIG. 8A. An intensity projection was extracted from the wall of the target and was plotted over time. The projection and extracted respiratory motion waveform are shown in FIG. 8B. Good visual agreement between the extracted motion pattern and the actual trajectory was observed. Partial saturation of the current and previous coronal slice groups is apparent within the navigator image.

Figure 9:
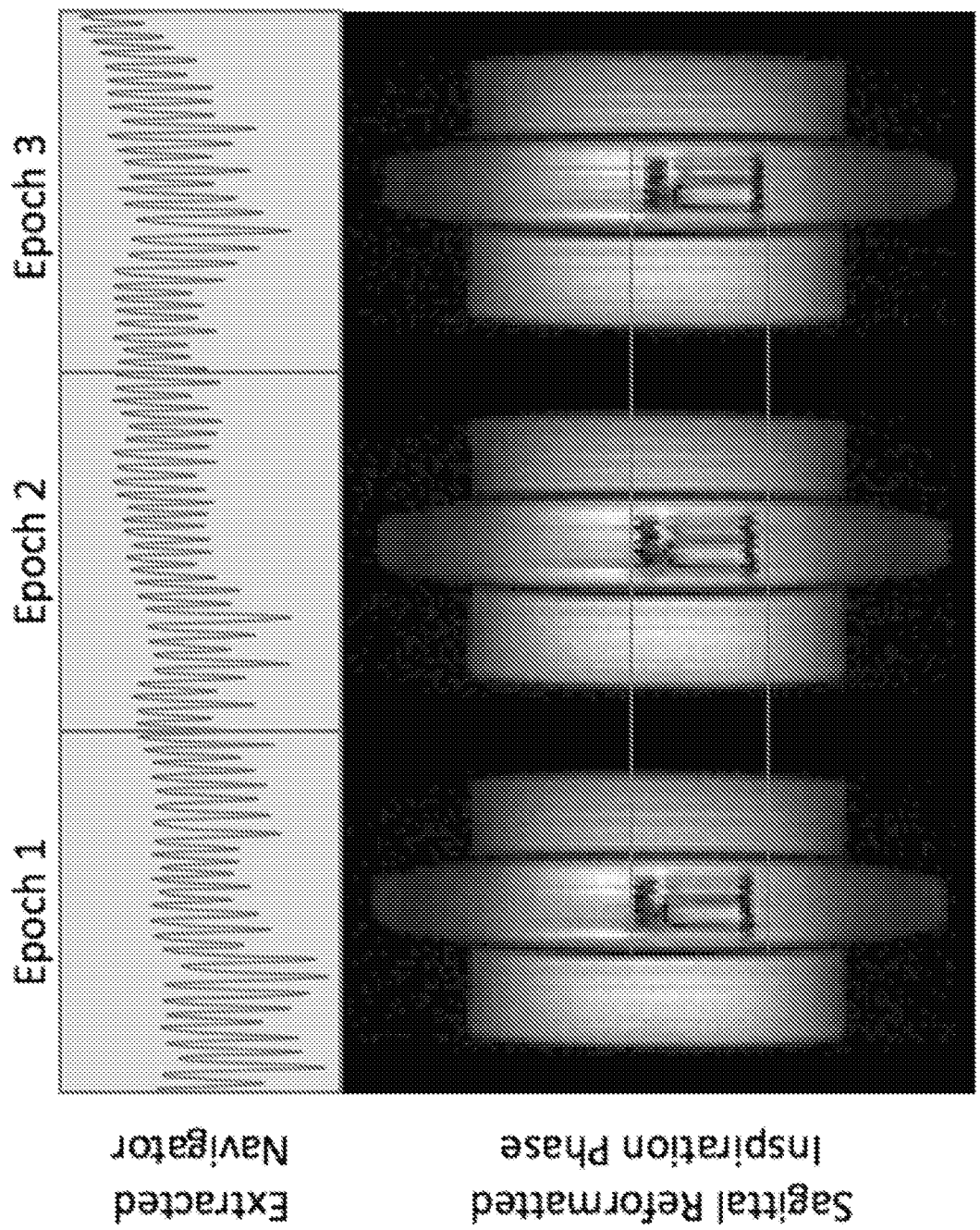
FIG. 9 shows a respiratory motion waveform used for amplitude-based sorting of the three 4D-MRI epochs (top), and sagittal reformats of the inspiratory phase of each 4D-MRI epoch (bottom). The red lines emphasize the variation in the target position within the same respiratory phase bin. Within all epochs, small amounts of coronal interslice motion are observed.

A sagittal reformat of the bin at the end of inspiration for each of the three 4D-MRI epochs are shown in FIG. 9. The target position in each of these epochs is in a different position along the superior/inferior direction, as expected, due to the trend in the original patient motion waveform. The red lines in FIG. 9 are reference lines to visualize the difference in target position in the different epochs. Slight slice-mismatch within each epoch is observed.

Figure 10:
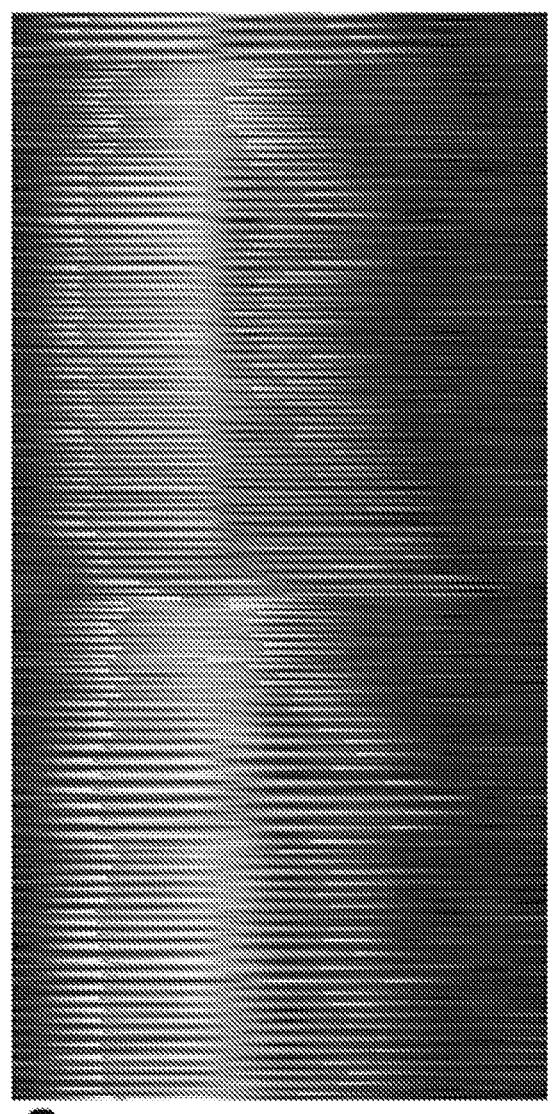
FIG. 10A is another example of a sagittal tracking, or navigator, image.
FIG. 10B is an intensity projection over time taken through part of the liver and extracted respiratory waveform (red).
Figure 10:
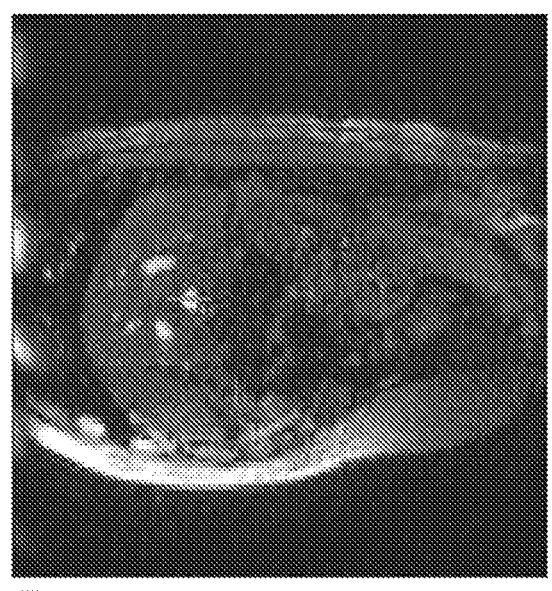

An example in vivo sagittal navigator image is shown in FIG. 10. Due to the high levels of acceleration, the image has a relatively low signal-to-noise ratio. However, sufficient contrast is present to visualize the liver and kidneys, and to extract a respiratory waveform to be used for data sorting.

Figure 11:
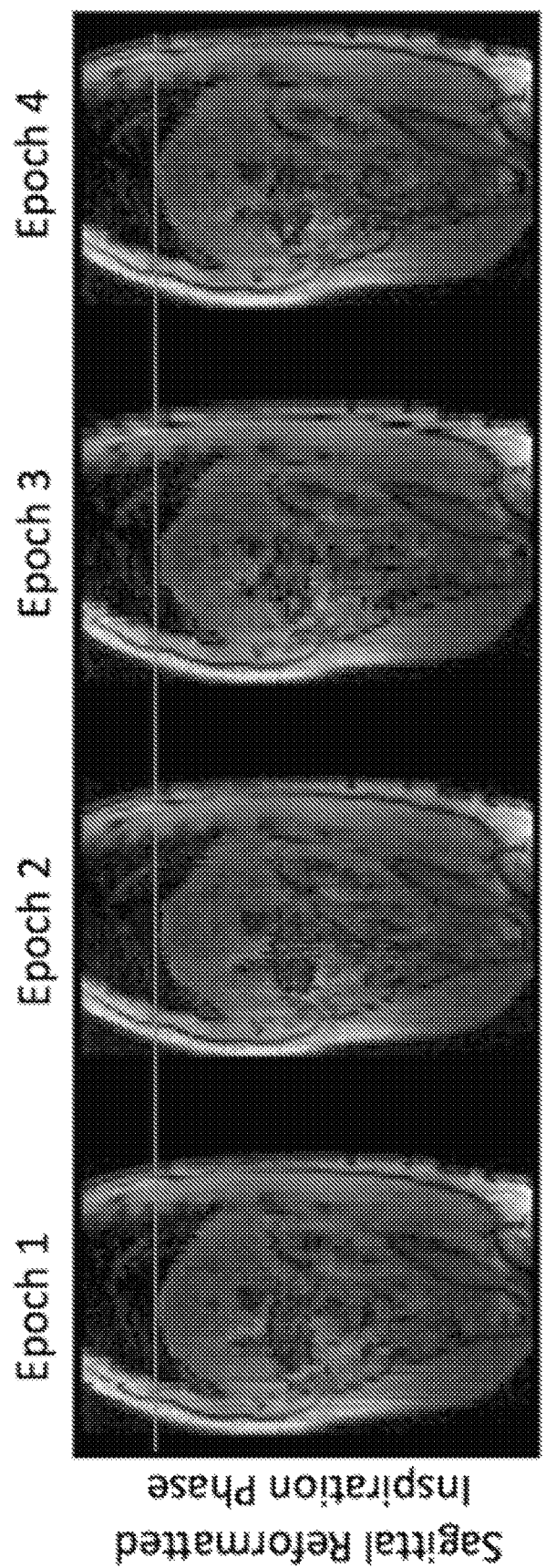
FIG. 11 depicts sagittal reformats of the end-of-inspiration phase for each of the four 4D-MRI epochs from the 1PL-4D-SOPI volunteer scan obtained in an example study described in the present disclosure.
Figure 12:
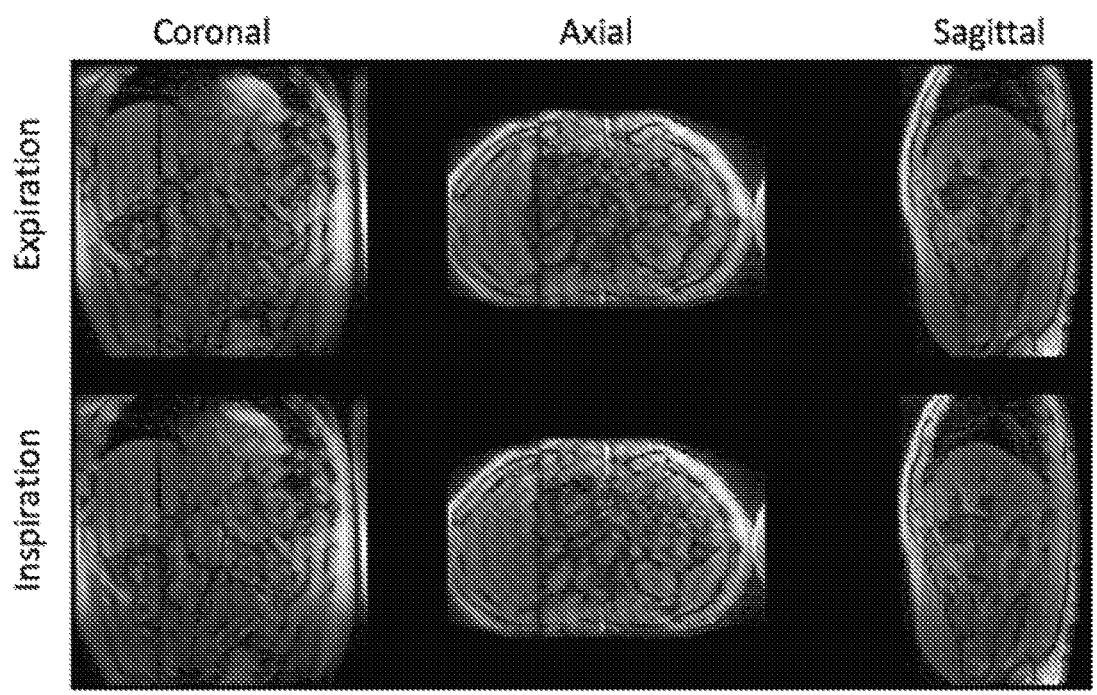
FIG. 12 shows images of expiration (top) and inspiration (bottom) phases in three orthogonal views of Epoch 1 of the human volunteer obtained in an example study described in the present disclosure.

A sagittal reformat of the inspiratory phase of each of the four epochs for the 1PL-4D-SOPI volunteer scan are shown in FIG. 11. As seen by the red reference line, the peak position of the liver at the end of inspiration remains relatively constant throughout all epochs. Visually, there is enough contrast in the images to delineate the liver and right kidney. In FIG. 12, views of the first epoch at the end of expiration and inspiration for three orthogonal planes are shown.

Following the calculation of the 4D-MRI epochs (5 bins×3 epochs), the total amount of time spent in each bin throughout the 7.5-minute delivery was determined from the position of the target in the navigator image. The fractions of time spent in each epoch and bin were used to scale the full 3200 MU dose distribution on each epoch/bin prior to aligning and accumulating them.

Figure 13:
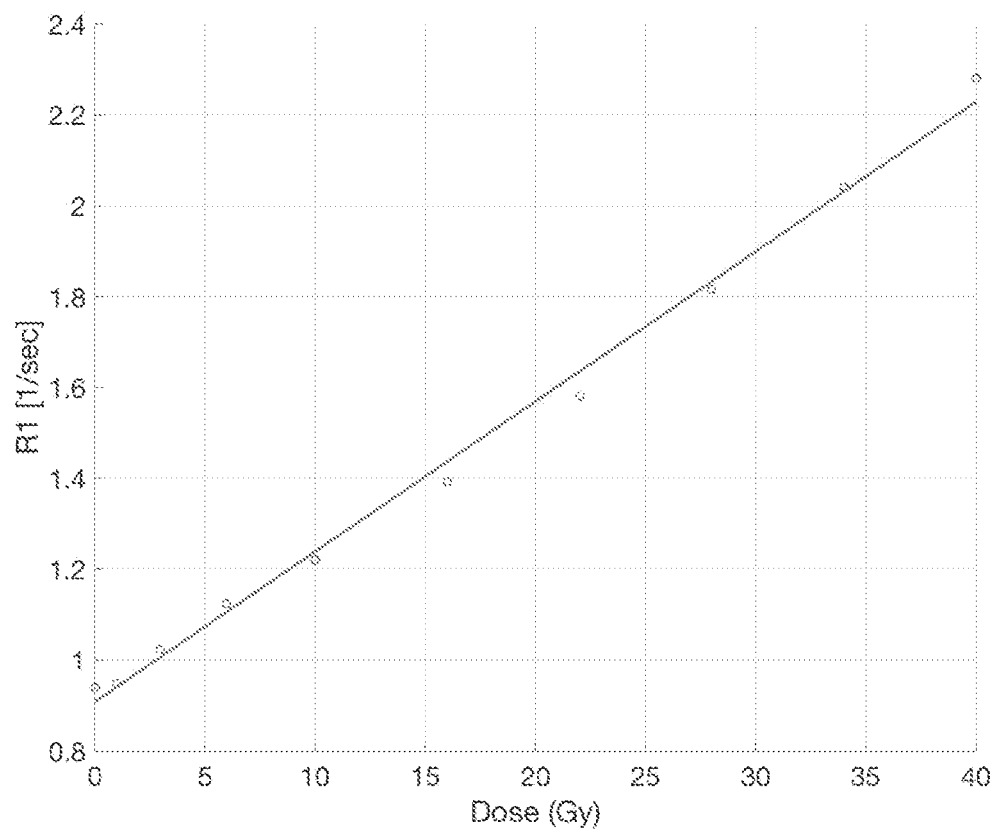
FIG. 13 is a plot of longitudinal relaxation rate as a function of dose for calibration vials filled with Fricke gel and treated to different doses.

FIG. 13 shows the longitudinal relaxation rate (1/T1) as a function of absolute dose for the ten calibration vials. The R1 vs dose line of best fit is given as, $$R_1 = 0.033(\text{Dose}) + 0.908 \tag{13}$$

Here, the dose in cGy is calculated using the longitudinal relaxation rate in units of $\sec^{-1}$. The $R^2$ value of linear fit was 0.995.

Figure 14:
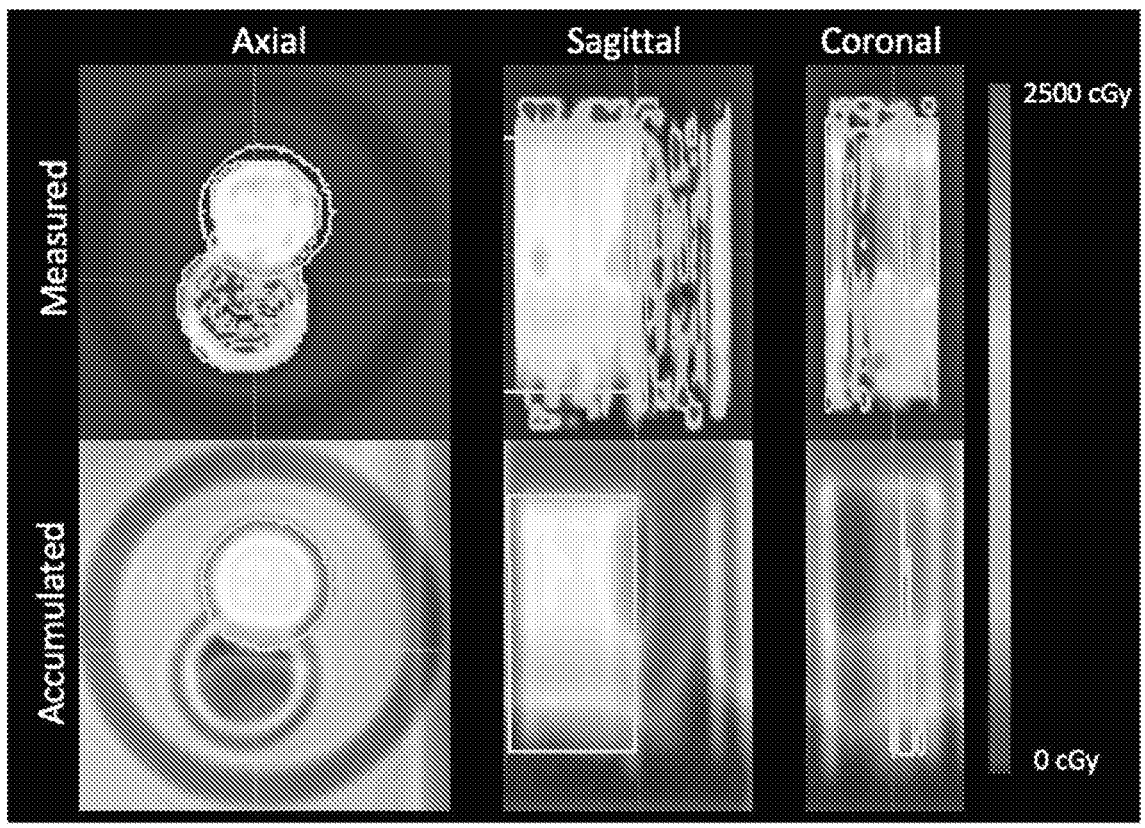
FIG. 14 shows measured dose distributions obtained via $R_1$ mapping and the accumulated dose distribution calculated in MIM of a treated dynamic phantom motion target.

Following the calibration experiment, the relationship between Dose and $R_1$ was applied to the 3D $R_1$ map acquired on the treated "pancreas" and "duodenum" target. The 3D dose distribution measured via the Fricke gel and the accumulated dose calculated in MIM are shown in FIG. 14. The expected effects of the electron return effect at the air/gel interface are observed in both the calculated and measured dose distributions. Also, blurring in the distributions along the superior/inferior direction due to motion is apparent.

Figure 15:
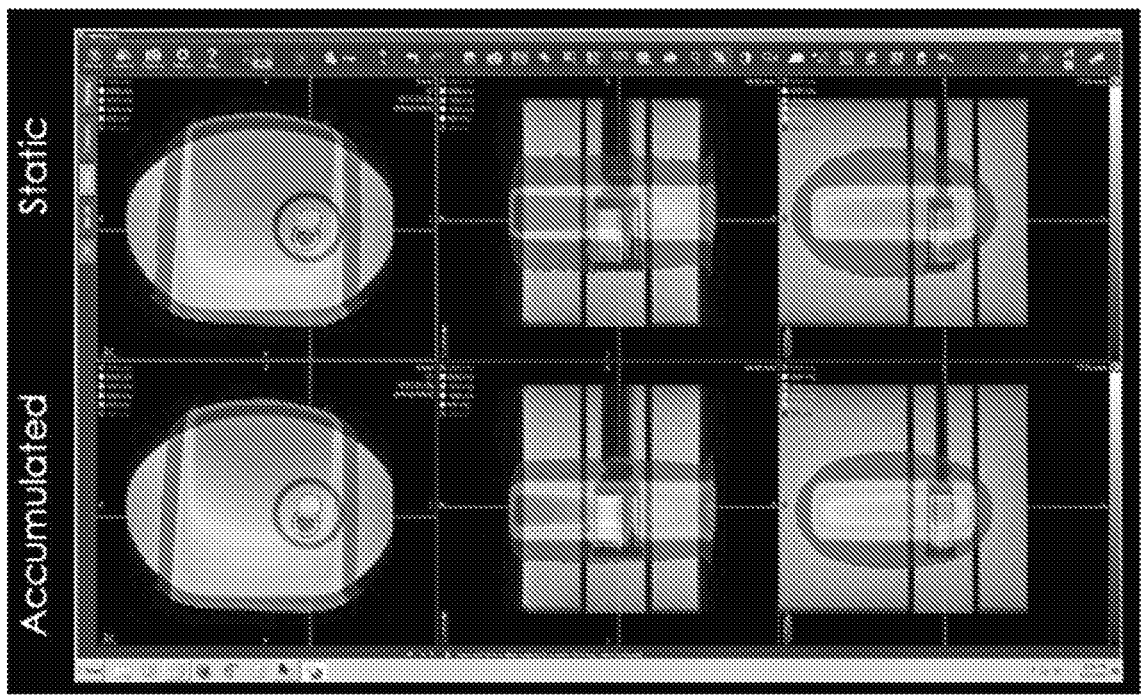
FIG. 15 shows static and accumulated dose distributions. The static distribution was calculated from delivery of 3200 MU on a single volume, and the accumulated is the sum of 15 dose distributions calculated on different MR volumes.

The difference between the accumulated dose distribution and the static distribution, with which the full 3200 MU was calculated on a single reference volume, can be visualized in FIG. 15. In the accumulated dose distribution, the dose in the target is less than that of the static distribution, and it is more blurred along the superior/inferior direction due to the motion of the phantom throughout the experiment.

Thus, described here are methods for acquiring respiratory phase resolved 4D-MRI volumes based on the simultaneous orthogonal plane imaging (SOPI) pulse sequence. The 4D-SOPI method can be used to acquire data and reconstruct a new 4D volume (4 bins) with good temporal resolution, such as every 2-3 minutes. A tracking, or navigator, slice can be acquired continuously in at least one orthogonal plane. The tracking, or navigator, images can be used for gating, tracking, trailing, and for sorting the concurrently acquired 4D imaging slices in a plane orthogonal to the navigator plane.

By generating 4D-MRI epochs throughout a treatment fraction, average respiratory phase volumes can be generated to adapt to changes in the patient breathing waveform, and also to capture anatomical changes due to dynamic filling and drifting (e.g., from the patient relaxing their back muscles during treatment). In an example study, an irregular breathing pattern was intentionally played out on a dynamic motion phantom while 4D-SOPI data were acquired. The drift in the average position of the target over time was apparent in the reconstructed images. This capability is crucial for obtaining accurate 3D volumes for dose accumulation.

As seen by slice mismatch in both the phantom and in vivo images, small variations in the motion state can exist within each bin. Using more bins would reduce this effect at the expense of requiring the interpolation of more slices that were not filled in each bin. As currently implemented, the image sorting takes place after obtaining magnitude coil-combined images. Image quality could be improved in some implementations by performing complex averaging of slices in the same location shuffled into the same bins.

A simple beam model was used to validate the use of the 4D-SOPI for dose accumulation in example studies using the methods described in the present disclosure. The relative length of the treatment fraction spent in each of the phases within each of the 4D-MRI epochs were used to weight the dose calculated on each respective 3D volume. For more complicated treatments (i.e. rotational delivery or step-and-shot IMRT), this simple linear weighting may not be accurate. Rather, a method which generates a 3D volume for every frame of the cine acquisition could be used. If organ filling motions are ignored, a unique bin for every frame could be generated by reshuffling data from the entire acquisition. Dose could then be calculated on every frame.

In the studies mentioned above, the "intrafraction" motion was calculated on a scanner separate from the Linac. The methods described here can advantageously be used on an integrated MR-Linac for true intrafraction motion assessment. This will also eliminate any setup uncertainties associated with moving the phantom between systems, or any timing delays between the start of the motion and the start of the imaging/treatment.

For dose accumulation on MR-gRT systems, the use of 4D-SOPI is beneficial due to its ability to provide cine images for tracking and gating while simultaneously generating serial 4D-MRI epochs that capture variations in anatomy over the course of a treatment fraction.

As described, 4D-SOPI combines in-plane and through-plane acceleration to maintain a fast frame rate while efficiently scanning slices in the 4D imaging plane. Due to g-factor noise enhancements, these acceleration factors may in some instances inhibit the acquisition of thin-slice isotropic resolution 4D-MRIs. An isotropic 4D-MRI may be desirable to minimize registration errors when accumulating reconstructed dose.

The 4D-SOPI techniques described in the present disclosure can be adapted to generate super-resolution ("SR") 4D images. As one non-limiting example, 4D-SOPI can be used for the simultaneous acquisition of prospective real-time orthogonal cine images and retrospective construction of serial, isotropic, 4D-MRI images. The SOPI method also has the additional advantage that orthogonal cine slices can be acquired in a time-locked fashion, which leads to improvements in motion estimation when compared with interleaved-slice cine imaging.

Using 4D-SOPI, cine imaging can be performed in two planes while simultaneously acquiring 4D imaging slices in both planes. The thickness of the slices in each plane can be suitable to maintain a reasonable signal-to-noise ratio ("SNR") after parallel imaging separation of the aliased slices. With the 4D-MRI volumes acquired in two planes, a super resolution reconstruction can be applied to reconstruct isotropic resolution volumes at each respiratory phase without acquiring images at a thin slice resolution.

Many super-resolution methods exist for combining multiple low resolution datasets with different spatial information to create a high resolution dataset. These super-resolution algorithms are generally applicable to 2D low resolution acquisitions with offset slice locations or multi-orientation low resolution acquisitions, but may not be directly applicable to 2D low resolution acquisitions acquired with shifted in-plane fields-of-view. The super-resolution volumes are typically reconstructed from multi-orientation low resolution volumes, making super-resolution methods advantageous for combining orthogonal 4D-MRI datasets.

Figure 16:
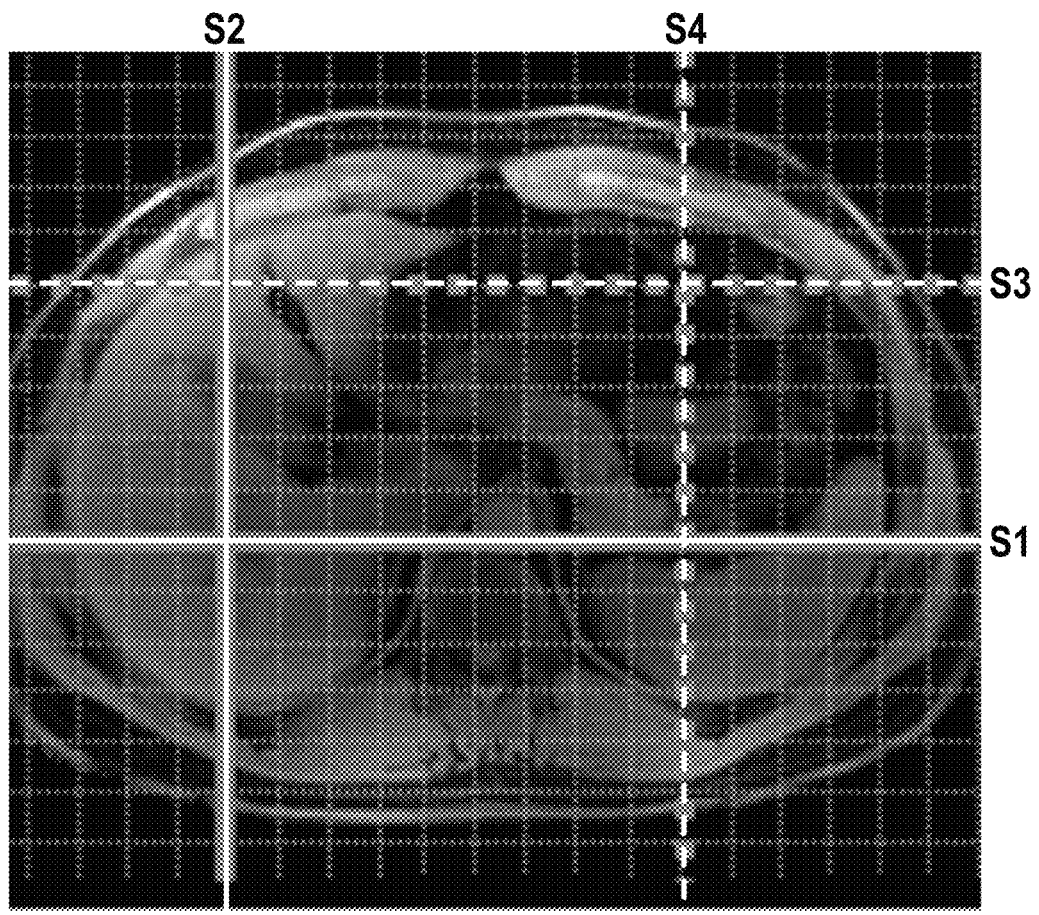
FIG. 16 shows an example 4D-SOPI imaging scheme in which a first slice group parallel with a first imaging plane and a second slice group parallel with a second imaging plane that is orthogonal to the first imaging plane are both excited within each TR. In each slice group, one of the slices remains fixed (e.g., a cine slice) while the others are dynamically changed in subsequent time frames.
Figure 17:
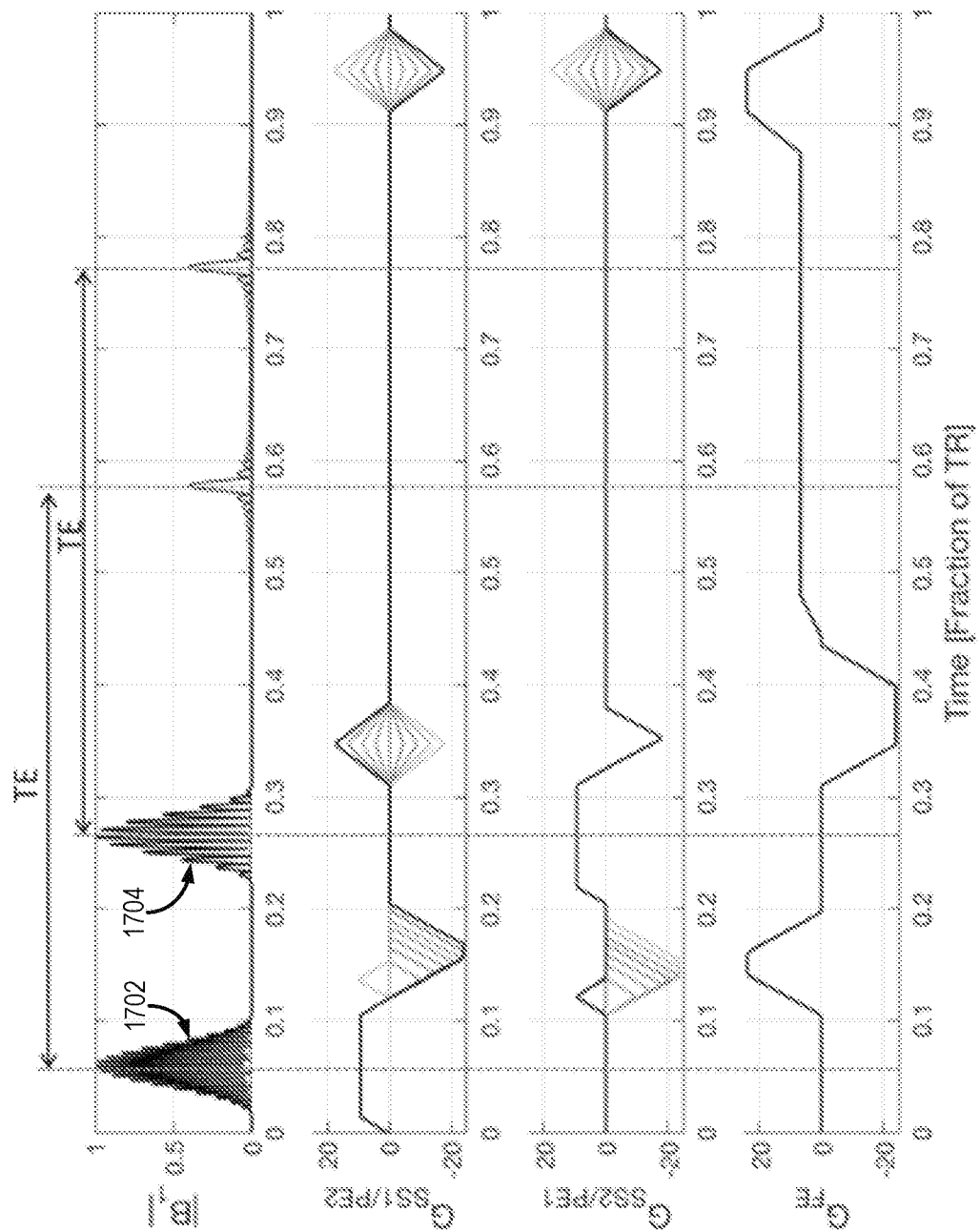
FIG. 17 is an example of a SOPI pulse sequence with equal echo times ("ETE"). In this example, the orthogonal slice packets are acquired with equal echo times and are separated via a SIR readout. A first multiband RF pulse is played out to excite slices parallel with a first imaging plane and a second multiband RF pulse is used to excite slices that a parallel with second imaging plane that is orthogonal to the first imaging plane.

The SR-4D-SOPI acquisition scheme and pulse sequence diagram are shown in FIGS. 16 and 17, respectively. In this example, an equal echo-time ("ETE") variant of a SOPI pulse sequence is used. As shown in FIG. 17, two consecutive multiband RF pulses 1702, 1704, are used to excite a pair of slices in each of two orthogonal planes, as shown in FIG. 16. For instance, the first multiband RF excitation pulse can excite slices S1 and S3 in a first slice group, and the second multiband RF excitation pulse can excite slices S2 and S4 in a second slice group. Slices S2 and S4 are each orthogonal to slices S1 and S3.

Balancing of the zeroth gradient moments, as described above, permits the simultaneous slice rewinding and phase encoding of slices along each axis prior to the echo time. A simultaneous image refocusing ("SIR") readout can be utilized, and the receiver bandwidth can be set to allow for the echo times of each slice group to be equal. One of the two slices excited along each axis remains fixed for cine imaging (e.g., slices S1 and S2 in FIG. 16) while the other slice (or slices) along each axis dynamically changes position to acquire volumetric data. In this way, the imaging slice positions are modified relative to the cine imaging slices. The pair of slices along each axis can be excited in quadrature (i.e., with a 90° phase difference) to minimize interference between their signals and to further encode the data. As one example, multiband sinc RF pulses can be used and can be calculated on-the-fly since the RF pulse shape changes depending on the location of the imaging slice simultaneously acquired with the cine slice.

As indicated by the intersecting grid lines in FIG. 16, two orthogonal stacks of slices (e.g., sagittal and coronal) are prescribed in this example. Four slices are acquired in every frame. Within each orthogonal stack, a single navigator slice (solid bold) is acquired during every frame. The position of the imaging slices (dashed bold), which are acquired simultaneously with the navigator slices, changes from frame to frame. The imaging slices are retrospectively "binned" into respiratory phases based on the position of the anatomy within the navigator slices.

Information from the cine images can be used to derive a 1D navigator to bin the imaging slices concurrently acquired with each cine frame. To achieve this, an image intensity projection can be extracted from a sharp tissue boundary in every frame of the cine images. The center-of-mass of the image intensity along the projection can then be used as a 1D navigator for respiratory motion. The amplitude of the navigator can be divided into equally sized bins with respect to the signal amplitude. Each imaging slice corresponding to each point in the navigator waveform can then be sorted into the appropriate respiratory phase bin. If multiple slices in the same location exist within the same bin, the magnitude images can be averaged. In the context of dose reconstruction for MR-gRT, a copy of the appropriate 4D imaging phase corresponding to each frame of the cine acquisition can be created and time-stamped according to the frame rate. This information, along with beam delivery logs and gradient nonlinearity distortion-corrected 4D-MRI volumes, can be used to reconstruct dose.

Two examples of super-resolution reconstruction algorithms are described. Both example algorithms aim to solve the following least squares problem:

$$x = \operatorname*{argmin}_{x} \sum_{k=1}^{N} \|y_k - A_k x\|_2^2; \quad (14)$$

where, x is the super-resolution volume data vector to be reconstructed, and y is a vector of the acquired low resolution multislice 2D volumes. The index, k, counts through the low resolution volumes. In the example described above with respect to FIG. 16, N=2 for the sagittal and coronal volumes. The model, A, is a matrix that maps the reconstructed isotropic data vector to the space of each acquired orthogonal volume. This model matrix includes a geometric transformation to match orientations and origins of the acquired low resolution orthogonal volumes (G), blurring to model a Gaussian point spread function (B), and a down-sampling and cropping operator (D):

$$A_k = D_k B_k G_k \quad (15).$$

The matrix, A, can be represented as a sparse matrix to conserve memory and reduce computation time.

One example of a super-resolution reconstruction algorithm is an iterative back-projection ("IBP") method. This method begins with an initial guess and uses the difference between the forward propagation of the model and the acquired low resolution data to update the guess iteratively. One example implementation of IBP is similar to the steepest descent method:

$$x^{(i+1)} = x^{(i)} + \sum_{k=1}^{N} A_k^T (y_k - A_k x^{(i)}). \quad (16)$$

Regularized least squares methods in super-resolution reconstruction aim to better condition the inverse problem in Eqn. (14). One such approach is to impose an $\ell_1$-regularization penalty on the total variation ("TV") of the volume in three dimensions. This method can promote a reduction of noise while minimizing blurring of edges. This regularized problem is posed as:

$$x = \operatorname*{argmin}_{x} \sum_{k=1}^{N} \|y_k - A_k x\|_2^2 + \lambda \|Tx\|_1; \quad (17)$$

where, T, represents the sparsifying TV transform, implemented as a finite difference in image intensity in three dimensions. The scalar regularization parameter, λ, allows for tradeoff between data consistency and the TV in the super-resolution volume. This problem can be solved via conjugate gradient ("CG") methods. For both of these example algorithms, the super-resolution reconstruction can be initialized with the average of the low resolution sagittal and coronal volumes.

The preceding examples show that 4D-SOPI can be implemented to permit simultaneous acquisition of cine and 4D-MRI in two orthogonal planes. The cine imaging data can serve two purposes. First, these data can be used for prospective, real-time, intrafraction motion management during MR-gRT. Second, these data can be used to retrospectively sort the concurrently acquired 4D-MRI slices into appropriate respiratory phase bins, as described above. The simultaneous acquisition of multi-respiratory phase 3D volumes enables retrospective, super-resolution reconstructions of isotropic 4D-MRI epochs.

In some examples, to achieve appropriate volumetric slice coverage without aliasing along the phase encoding direction, large fields-of-view may be necessary. Coupled with a relatively small matrix size (e.g., 128×128), the resulting super-resolution volumes can be between 2.5 mm and 2.9 mm isotropic. These resolutions are on the order of typical grid sizes employed for radiation dose calculations. In some other example, a finer resolution may be desired if more accurate delineations are to be made. In these instances case, higher acceleration factors may be used to maintain a frame rate reasonable for motion monitoring while improving resolution.

In the SR-4D-SOPI examples described above, a single navigator slice and a single imaging slice are acquired simultaneously in each imaging plane. Small amounts of residual aliasing may sometimes be observed in the images reconstructed with algorithms such as the phase-constrained 2D SENSE-GRAPPA algorithm. If higher density phased-array coils are used for signal reception, it may be possible to further reduce these artifacts, and the through-plane acceleration factor could perceivably be increased to enable three simultaneous slices per axis. These implementations can provide additional flexibility to tailor the acquisition to the particular target type.

For example, MR-gRT of the pancreas may benefit from real-time motion monitoring of the pancreas and the duodenum. Adding additional cine slices intersecting the lung-liver interface would allow the navigator information to be obtained in addition to the real-time motion monitoring of the targets and OAR.

Figure 18:
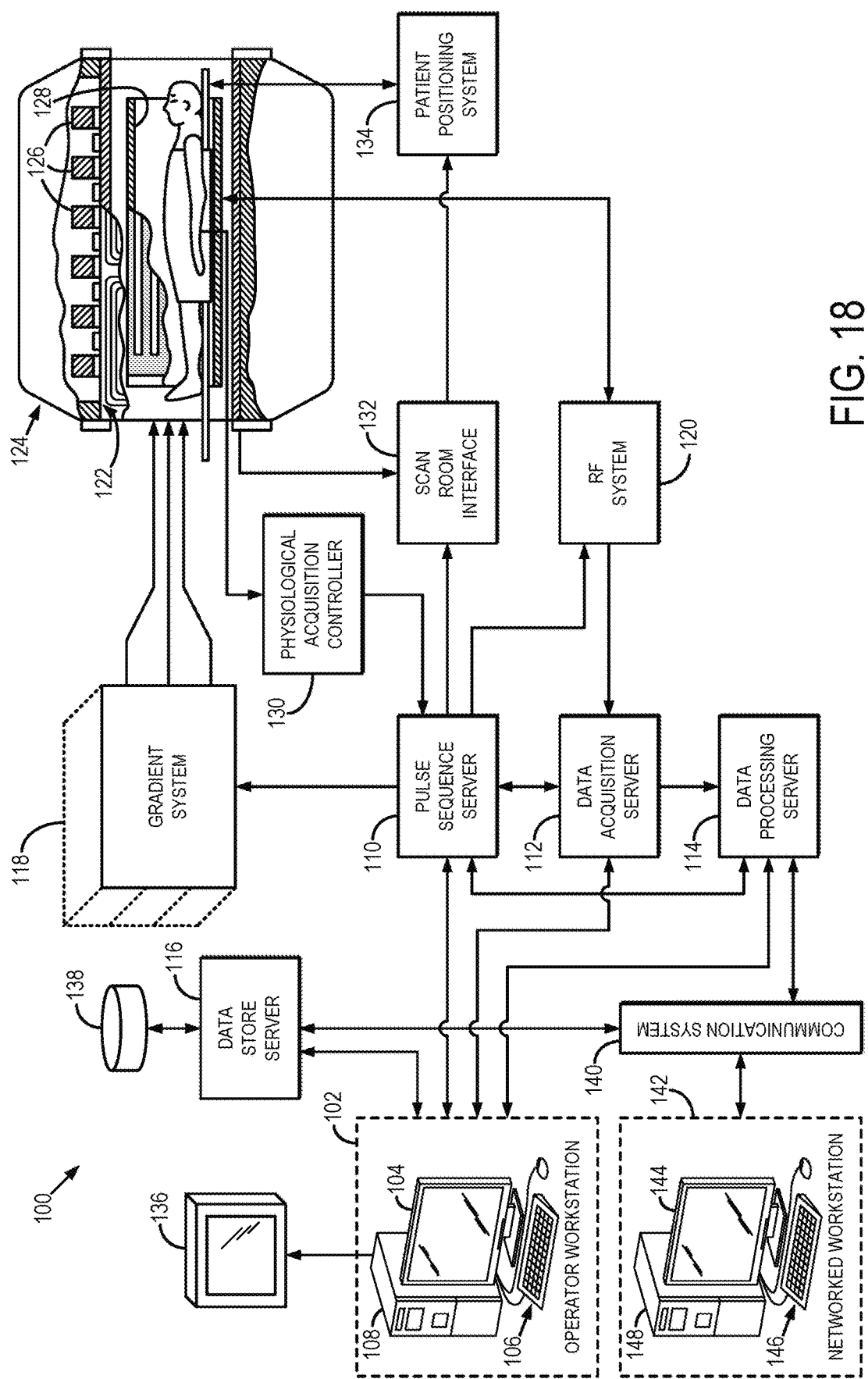
FIG. 18 is a block diagram of an example magnetic resonance imaging ("MRI") system that can implement the methods described in the present disclosure. In some implementations, the MRI system can form a part of an integrated MRI linear accelerator ("MRI-Linac") system.

Referring particularly now to FIG. 18, an example of an MRI system 100 that can implement the methods described here is illustrated. In some implementations, the MRI system 100 can form a part of an integrated MRI linear accelerator ("MRI-Linac") system. The MRI system 100 includes an operator workstation 102 that may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \quad (18);$$

and the phase of the received magnetic resonance signal may also be determined according to the following relationship:

$$\varphi = \tan^{-1}\left(\frac{Q}{I}\right). \quad (19)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

The present disclosure has described one or more preferred embodiments, and it should be appreciated that many equivalents, alternatives, variations, and modifications, aside from those expressly stated, are possible and within the scope of the invention.

The invention claimed is:

1. A method for producing images of a subject using a magnetic resonance imaging (MRI) system, the steps of the method comprising:
   (a) acquiring data from a volume in the subject with the MRI system using a pulse sequence in which the data are simultaneously acquired in each repetition time period of the pulse sequence as first data from a first slice and second data from a second slice that is orthogonal to the first slice, wherein the pulse sequence is repeated for a number of repetition time periods during which a position of the first slice remains static and a position of the second slice is changed such that the second data are acquired from different slices in the volume that are each orthogonal to the first slice;
   (b) reconstructing a series of first images from the first data; and
   (c) reconstructing a series of second images from the second data,
   wherein the pulse sequence comprises:
   simultaneously acquiring the first data from the first slice and from a third slice that is parallel with the first slice, wherein a position of the third slice is changed in each of the number of repetition time periods; and
   simultaneously acquiring the second data from the second slice and from a fourth slice that is parallel with the second slice, wherein a position of the fourth slice remains static in each of the number of repetition time periods,
   wherein the first slice corresponds to a first navigator slice, and the fourth slice corresponds to a second navigator slice, wherein the first navigator slice is used to retrospectively bin images acquired at the second slice into corresponding motion bins, and wherein the second navigator slice is used to retrospectively bin images acquired at the third slice into corresponding motion bins.

2. The method as recited in claim 1, further comprising estimating motion parameters from the series of first images, wherein the motion parameters indicate motion of the subject that occurred while the data were acquired from the volume.

3. The method as recited in claim 2, further comprising compensating the series of second images using the motion parameters estimated from the series of first images.

4. The method as recited in claim 1, further comprising calculating an accumulated dose in the volume based on the series of second images.

5. The method as recited in claim 4, further comprising estimating motion parameters from the series of first images, wherein the motion parameters indicate motion of the subject that occurred while the data were acquired from the volume, and compensating the series of second images using the motion parameters estimated from the series of first images such that the accumulated dose calculated from the series of second images is compensated for the motion of the subject.

6. The method as recited in claim 1, wherein the pulse sequence comprises simultaneously acquiring the second data from a plurality of second slices in each said repetition time period, wherein each of the plurality of second slices are parallel to each other and orthogonal to the first slice.

7. The method as recited in claim 6, wherein the pulse sequence comprises a multiband radio frequency (RF) pulse to simultaneously excite spins in the plurality of second slices in each said repetition time period.

8. The method as recited in claim 1, wherein the pulse sequence comprises a multiband radio frequency (RF) pulse to simultaneously excite spins in the second slice and the third slice in each said repetition time period.

9. The method as recited in claim 1, wherein the pulse sequence comprises a multiband radio frequency (RF) pulse to simultaneously excite spins in the first slice and the third slice in each said repetition time period.

10. The method as recited in claim 1, wherein the first data are acquired from a first echo in each said repetition time period and the second data are acquired from a second echo time in each said repetition time period.

11. The method as recited in claim 10, wherein the first echo occurs before the second echo.

12. The method as recited in claim 10, wherein the first echo occurs after the second echo.

13. The method as recited in claim 10, wherein the first echo time and the second echo time are equal.

14. The method as recited in claim 10, wherein the first echo time and the second echo time are not equal.

15. The method as recited in claim 1, wherein the series of first images is reconstructed using a first reconstruction algorithm and the series of second images is reconstructed using a second reconstruction algorithm that is different from the first reconstruction algorithm.

16. The method as recited in claim 1, further comprising calculating an accumulated dose in the volume based on the series of second images and updating a radiation treatment plan based on the accumulated dose.

17. The method as recited in claim 1, further wherein the data are acquired while a radiation treatment is being delivered to the subject, and further comprising monitoring the series of first images to detect a change in position of an anatomical target and stopping the radiation treatment when the change in the position of the anatomical target is detected.

18. The method as recited in claim 17, wherein the anatomical target is an organ-at-risk (OAR) and the change in position of the OAR is a movement of the OAR into a radiation field of the radiation treatment.

19. The method as recited in claim 17, wherein the anatomical target is a planned treatment volume (PTV) and the change in position of the PTV is a movement of the PTV outside of a radiation field of the radiation treatment.

20. The method as recited in claim 1, wherein the pulse sequence comprises a first multiband radio frequency (RF) pulse to simultaneously excite spins in the first slice and the third slice in each said repetition time period, and a second multiband RF pulse to simultaneously excite spins in the second slice and the fourth slice in each said repetition time period.

21. The method as recited in claim 1, wherein each motion bin corresponds to a different respiratory phase.

22. The method as recited in claim 1, further comprising reconstructing a series of third images from the series of first images and the series of second images, wherein images in the series of third images have a higher spatial resolution than images in both the series of first images and the series of second images.

23. The method as recited in claim 22, wherein the series of third images is reconstructed using an iterative back projection super-resolution reconstruction.

24. The method as recited in claim 22, wherein the series of third images is reconstructed using an L1-regularization-based super-resolution reconstruction.

* * * * *